US011134965B2

(12) United States Patent
Gilbert

(10) Patent No.: US 11,134,965 B2
(45) Date of Patent: Oct. 5, 2021

(54) ADJUNCTIVE LOCALIZATION SYSTEMS AND DEVICES

(71) Applicant: Asia Pacific Medical Technology Development Company, Ltd, Pak Shek Kok (HK)

(72) Inventor: John R. Gilbert, Brookline, MA (US)

(73) Assignee: Asia Pacific Medical Technology Development Company, Ltd, Pak Shek Kok (HK)

( * ) Notice: Subject to any disclaimer, the term of this patent is extended or adjusted under 35 U.S.C. 154(b) by 1257 days.

(21) Appl. No.: 15/006,706

(22) Filed: Jan. 26, 2016

(65) Prior Publication Data

US 2017/0209159 A1 Jul. 27, 2017

(51) Int. Cl.
*A61B 17/22* (2006.01)
*A61B 17/3207* (2006.01)
*A61B 17/00* (2006.01)

(52) U.S. Cl.
CPC .......... *A61B 17/22* (2013.01); *A61B 17/3207* (2013.01); *A61B 2017/00477* (2013.01); *A61B 2017/22014* (2013.01); *A61B 2017/22054* (2013.01); *A61B 2017/22062* (2013.01); *A61B 2017/22067* (2013.01); *A61B 2017/22084* (2013.01)

(58) Field of Classification Search
CPC ............... A61B 17/22; A61B 17/3207; A61B 2017/00477; A61B 2017/22014; A61B 2017/22054; A61B 2017/22062; A61B 2017/22067; A61B 2017/22084; A61F 2/95
See application file for complete search history.

(56) References Cited

U.S. PATENT DOCUMENTS

| | | | |
|---|---|---|---|
| 4,445,892 A | 5/1984 | Hussein et al. | |
| 4,552,143 A | 11/1985 | Lottick | |
| 4,781,677 A | 11/1988 | Wilcox | |
| 4,911,163 A | 3/1990 | Fina | |
| 5,460,610 A | 10/1995 | Don Michael | |
| 5,833,650 A * | 11/1998 | Imran | A61M 25/1011 |
| | | | 604/509 |
| 6,071,233 A | 6/2000 | Ishikawa et al. | |
| 6,280,414 B1 | 8/2001 | Shah et al. | |
| 6,485,497 B2 | 11/2002 | Wensel et al. | |
| 8,182,422 B2 | 5/2012 | Bayer et al. | |
| 8,197,463 B2 | 6/2012 | Intoccia | |

(Continued)

FOREIGN PATENT DOCUMENTS

WO   2013/022853 A1   2/2013

OTHER PUBLICATIONS

Banka et al. "Dual-balloon progressive coronary dilatation catheter:design and initial clinical experience", Am Heart J, 127(2):430-5 (1994). Abstract Only.

(Continued)

*Primary Examiner* — Rebecca E Eisenberg
*Assistant Examiner* — John A Doubrava
(74) *Attorney, Agent, or Firm* — McCarter & English, LLP; Kia L. Freeman; Thomas F. Foley

(57) ABSTRACT

The present disclosure describes effector deployment systems and devices that can be coupled adjunctively to a shaft of a concentric cylinder system, to provide additional functionality during intravascular procedures.

29 Claims, 21 Drawing Sheets

(56) References Cited

U.S. PATENT DOCUMENTS

| | | |
|---|---|---|
| 2004/0243158 A1* | 12/2004 | Konstantino ....... A61M 25/104 606/159 |
| 2005/0137457 A1 | 6/2005 | Machida |
| 2005/0137647 A1 | 6/2005 | Wallace et al. |
| 2005/0267407 A1 | 12/2005 | Goldman |
| 2009/0318943 A1 | 12/2009 | Eidenschink et al. |
| 2010/0125164 A1 | 5/2010 | LaBombard |
| 2012/0289945 A1 | 11/2012 | Segermark |
| 2014/0214071 A1 | 7/2014 | Thomas |
| 2015/0230951 A1 | 8/2015 | Ai-Saadon |

OTHER PUBLICATIONS

International Search Report and Written Opinion for International Application No. PCT/US16/14877, dated Jan. 26, 2016.
Gobin, "MERCI Story: Making a Dream Come True", downloaded from http://www.radnet.ucla.edu/radweb/sections/endovascular/news/MERCI_Story.jsp, last accessed Nov. 3, 2015.
Gupta et al. "Endovascular Therapy for Acute Limb Ischemia", Endovascular Today, Sep. 2010, pp. 90-95.
Leahy-Patano, "Clot Removal Not a One-Size-Fits-All Therapy", Diagnostic and Interventional Cardiology, published May 19, 2009, 19 pages, downloaded from http://www.dicardiology.com/article/clotremovalnotonesizefitsalltherapy, last accessed Nov. 3, 2015.

\* cited by examiner

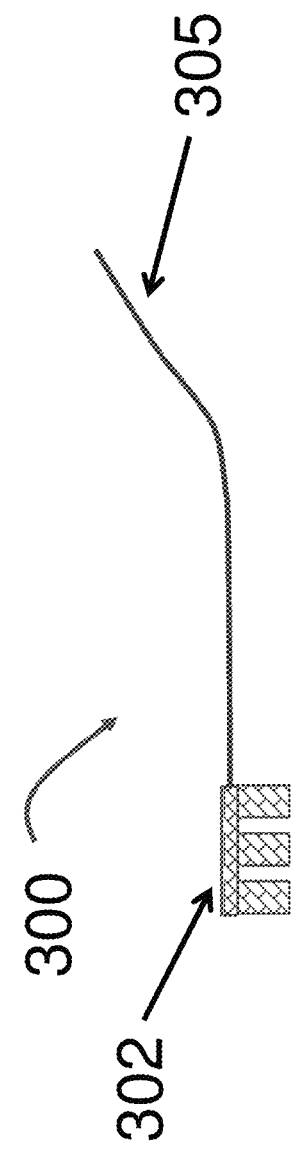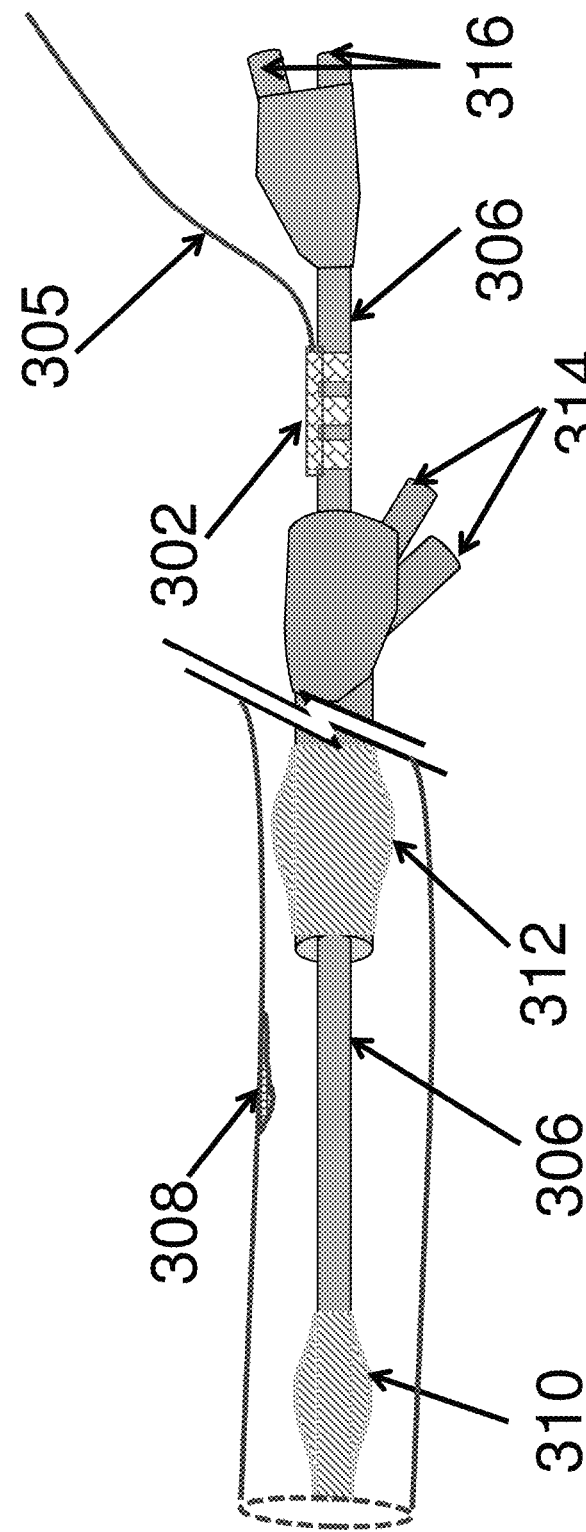
FIG. 3A
FIG. 3B

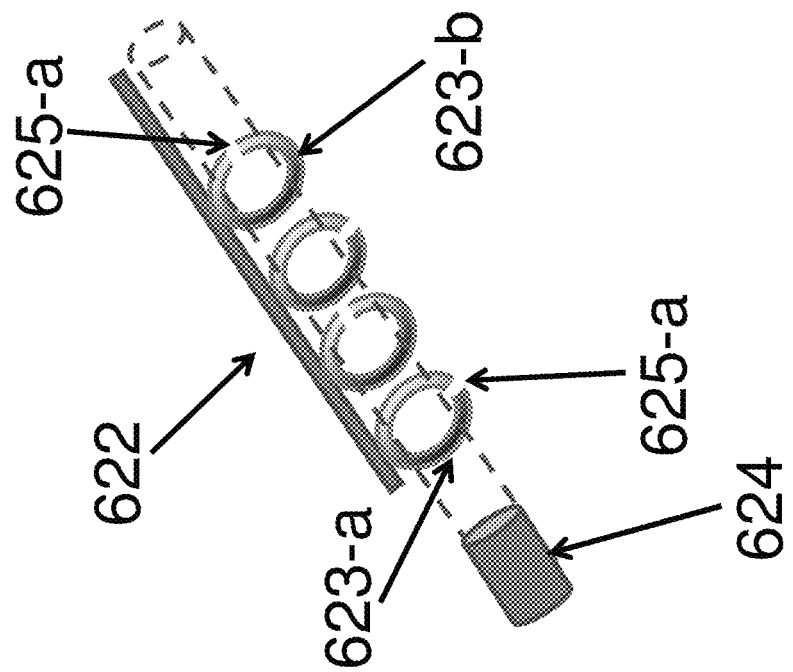
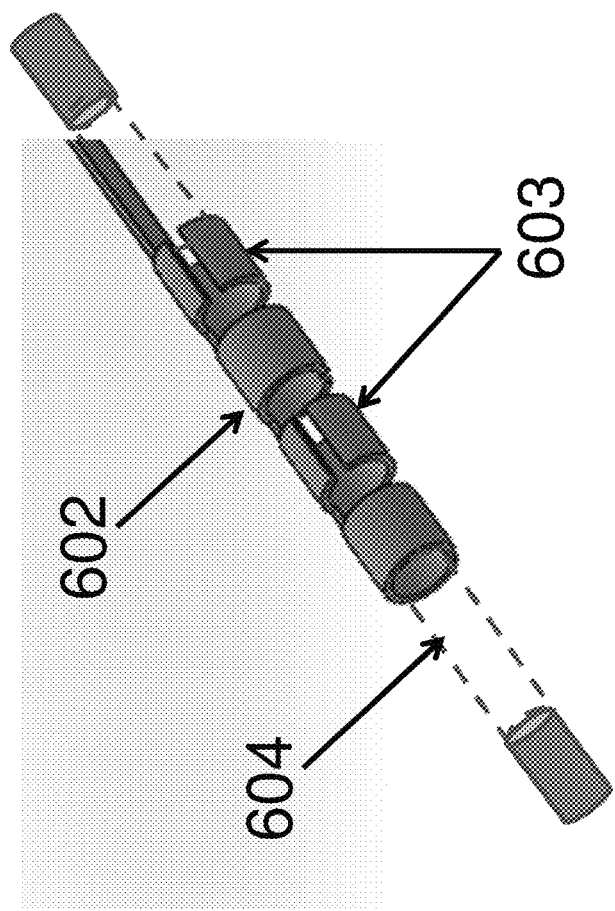
FIG. 6A
FIG. 6B

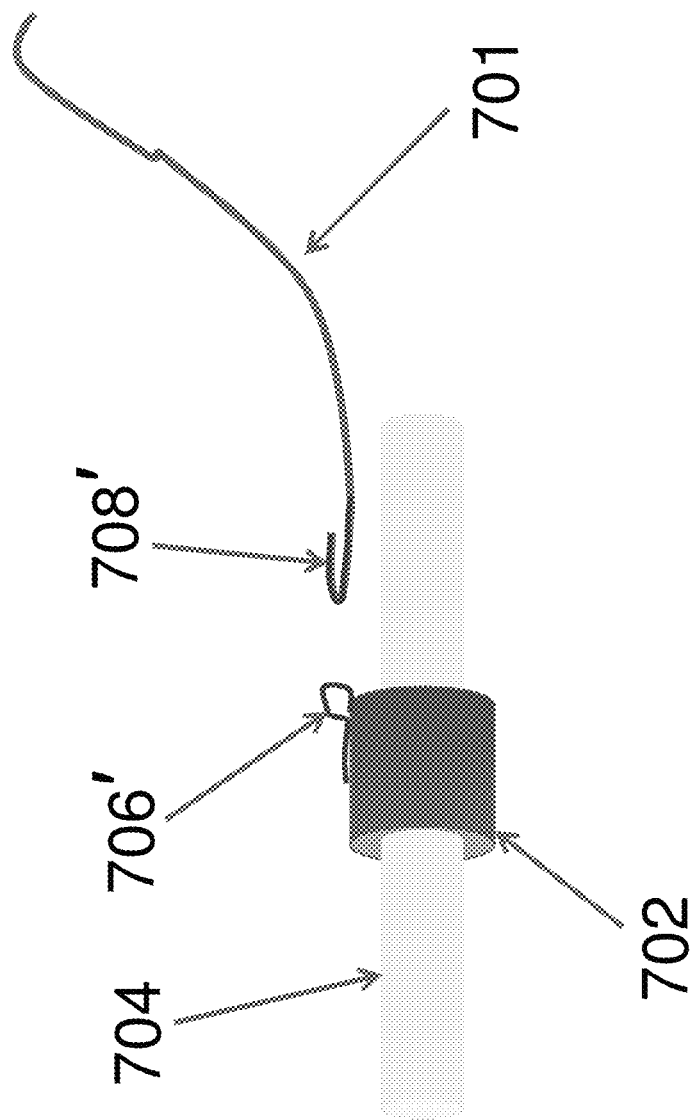

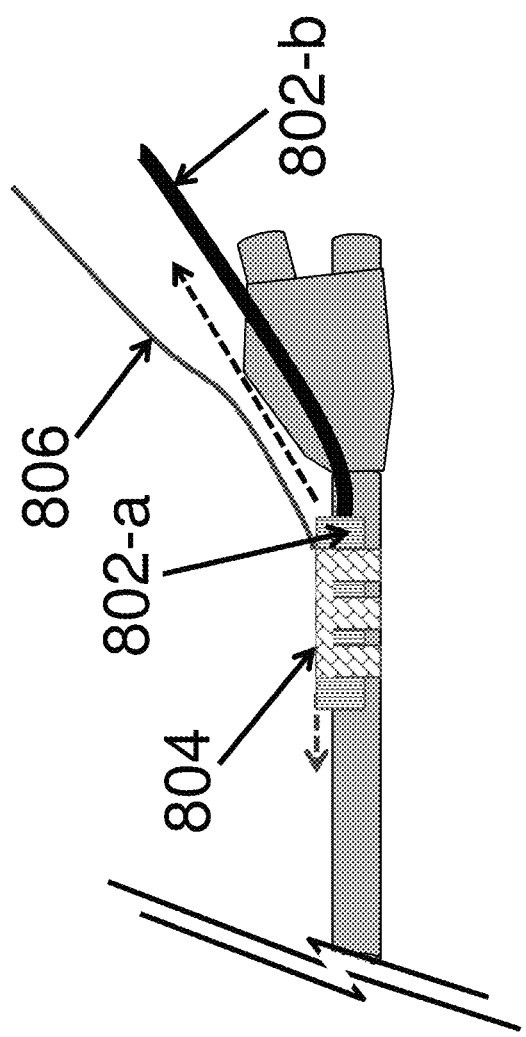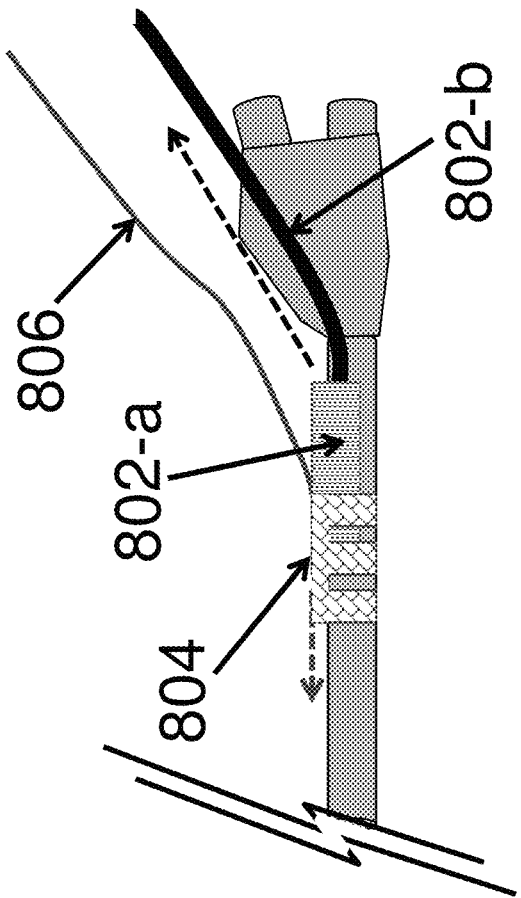
FIG. 8C
FIG. 8D

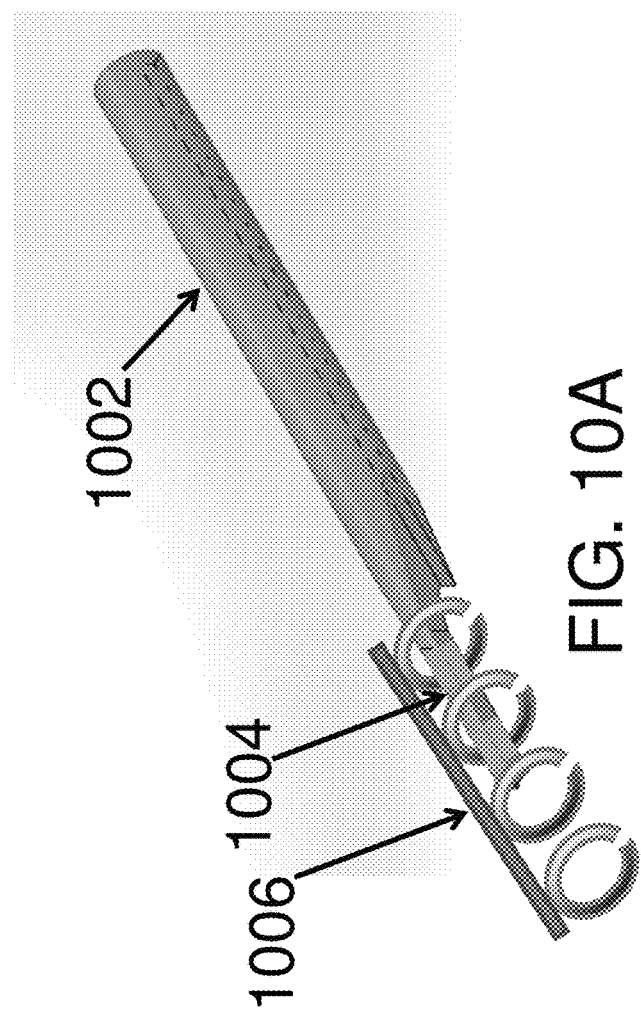
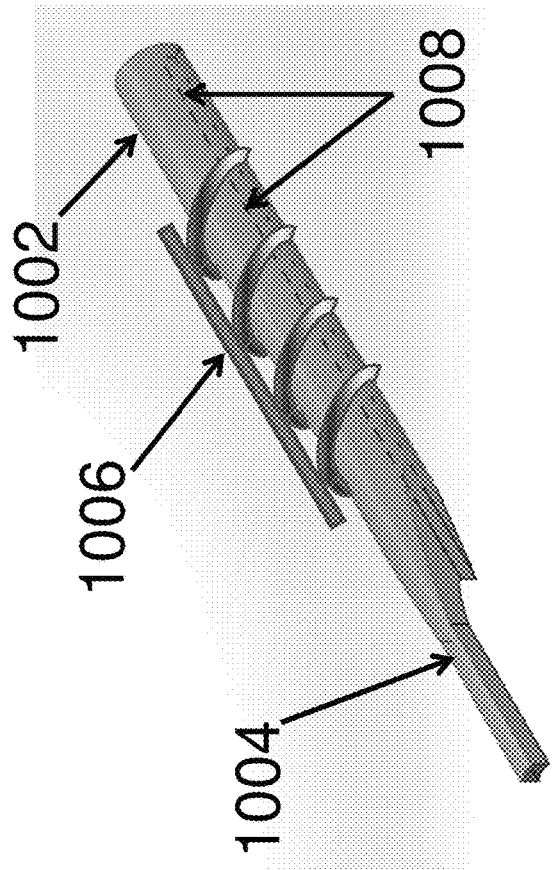
FIG. 10A
FIG. 10B

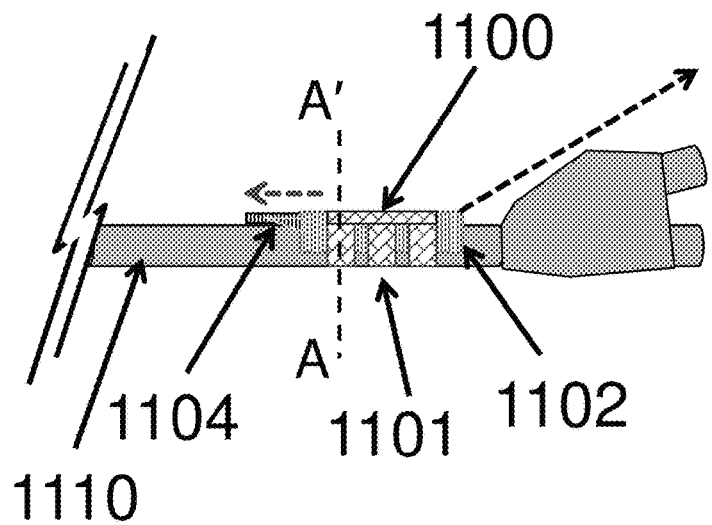
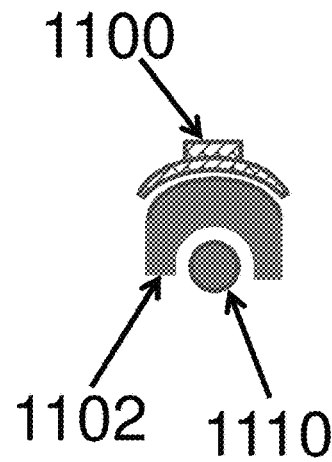
FIG. 11C(i)　　　　FIG. 11C(ii)
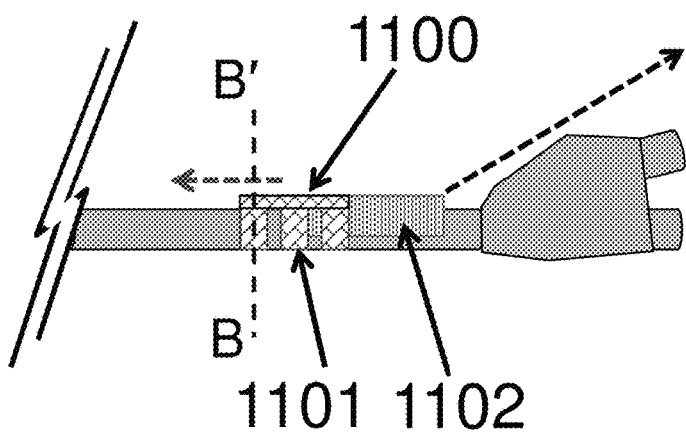
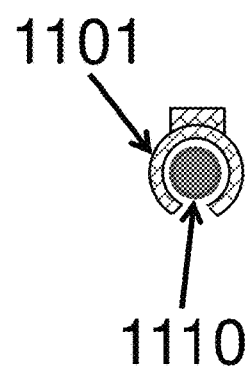
FIG. 11C(iii)　　　　FIG. 11C(iv)

ADJUNCTIVE LOCALIZATION SYSTEMS AND DEVICES

BACKGROUND

Many thromboembolic disorders, such as stroke, pulmonary embolism, peripheral thrombosis, atherosclerosis, and the like, are characterized by an occlusion of a blood vessel. The occlusion can be caused in a localized area of tissue by a clot which is viscoelastic and is comprised of platelets, fibrinogen and other clotting proteins. When an artery is occluded by a clot, tissue ischemia (lack of oxygen and nutrients) can develop. Failure to re-establish blood-flow can lead to the loss of limb, angina pectoris, myocardial infarction, stroke or even death. Occlusion of the venous circulation by thrombi can lead to blood stasis which can cause numerous problems. Re-establishing blood flow and removal of the thrombus is highly desirable.

Another localized problem is the presence of foreign bodies. Foreign bodies introduced into the circulation can be fragments of catheters, pace-maker electrodes, guide wires, and misplaced embolic material such as thrombogenic coils.

The design of many existing intravascular systems limit their capability to perform certain function on localized target areas of tissue, such as removal of thrombi, emboli, or foreign bodies, arterial or venous filtration, local drug or pharmaceutical agent administration, or other functions.

SUMMARY

There are concentric cylinder systems in the art that can be used to demark regions of tissue for performing a procedure. In an example concentric cylinder system, the ends of an outer cylinder and an inner cylinder can be used to demark a section of tissue, thereby creating a localized region of tissue for the performance of the procedure.

While such concentric cylinder systems can be used effectively to create the demarked sections of tissue, it can be difficult to introduce instruments in this localized demarked region for performing the procedure. For example, connections of other features at the proximal portion of these concentric cylinder systems can obstruct access along the shaft, making it very difficult to feed instruments to the localized demarked region. In addition, it can be difficult to control the pathway of a guidewire to remain substantially parallel to the shaft of the concentric cylinder system. For example, there is a risk that the guidewire can be diverted down a branch of the vasculature. This can result in misdirection of any instrument being fed along the guidewire towards the localized demarked region of tissue, as it may also be misdirected down that branch of the vasculature. There is a need for an adjunctive system that can be coupled to the proximal region of such concentric cylinder systems and fed along the shaft in a controlled manner to the localized demarked region of tissue Accordingly, the example systems, methods, and apparatus herein provide adjunctive system that can be easily deployed with an existing concentric cylinder system to provide additional functionality in localized area of tissue. In particular, the example systems, methods, and apparatus herein provide adjunctive devices that can be mounted to a concentric cylinder system for performing certain specialized, targeted procedures on localized target areas of tissue. The example adjunctive devices can be mounted to a shaft at a proximal portion of the concentric cylinder system, while the distal portion of the concentric cylinder system is positioned at a target region of interest in a tissue lumen. The example adjunctive systems disclosed herein are configured to be fed along the shaft of a concentric cylinder system in a controlled manner to the localized demarked region of tissue. The example adjunctive systems allow for a greater number and variety of procedures to be performed on tissue in a localized target zone.

The example adjunctive devices can be configured as a set of simplified devices to be used adjunctively to improve or modify treatments in a target zone established using a concentric cylinder system. As a non-limiting example, the target zone can be established by the length defined by the exposed inner cylinder of a concentric cylinder system.

An example adjunctive system herein can be configured, as non-limiting examples, for the removal of thrombi, emboli, or foreign bodies, arterial or venous filtration, local agent administration, or other functions during intravascular procedures.

The instant disclosure provides also example systems, devices, apparatus and methods that allow for coupling of an effector deployment system as an adjunctive feature to a concentric cylinder system.

Example systems, methods, and apparatus herein provide an effector deployment system that includes a mounting element configured to slidably couple to an inner shaft of a concentric cylinder system, and an effector component configured to couple to the mounting element at a proximal portion of the inner shaft and to perform a procedure on a portion of tissue proximate to a localized target zone that is between a distal tip of an outer cylinder and a distal tip of an inner cylinder of the concentric cylinder system.

An example method using the effector deployment system includes disposing the concentric cylinder system proximate to a localized target zone of tissue forming a lumen of a body, where the localized target zone is between a distal tip of an outer cylinder and a distal tip of an inner cylinder of the concentric cylinder system. The concentric cylinder system includes the inner shaft and the outer cylinder surrounding at least a portion of the inner shaft. The method further includes mounting an effector deployment system to a portion of the inner shaft, where the effector deployment system includes a mounting element configured to slidably couple to the inner shaft and an effector component coupled to the mounting element and configured to perform a procedure on a portion of tissue, applying a force to advance or retract the mounting element along at least a portion of the inner shaft in a region of the localized target zone.

Example systems, methods, and apparatus herein provide an effector deployment system the includes a mounting element configured to slidably couple to an inner shaft of a concentric cylinder system, an effector component configured to couple to the mounting element and to perform a procedure on a portion of tissue proximate to a localized target zone that is between a distal tip of an outer cylinder and a distal tip of an inner cylinder of the concentric cylinder system, and a feeder linkage configured to couple to a proximal portion of the mounting element and to apply a force to advance or retract the mounting element along at least a portion of the inner shaft.

An example method using the example effector deployment system includes disposing the concentric cylinder system proximate to a localized target zone of tissue forming a lumen of a body, such that the localized target zone is between a distal tip of an outer cylinder and a distal tip of an inner cylinder of the concentric cylinder system, and mounting an effector deployment system to a portion of the inner shaft. The effector deployment system includes a mounting element configured to slidably couple to the inner shaft, a feeder linkage coupled to the mounting element, and an effector component coupled to the mounting element and configured to perform a procedure on a portion of tissue. The example method further includes using the feeder linkage to apply a force to advance or retract the mounting element along at least a portion of the inner shaft in a region of the localized target zone.

Example systems, methods, and apparatus herein provide an effector deployment system that includes a cart configured to slidably couple to an inner shaft of a concentric cylinder system, an effector component configured to couple to the cart and to perform a procedure on a portion of tissue in a localized target zone, the localized target zone being between a distal tip of an outer cylinder and a distal tip of an inner cylinder of the concentric cylinder system, a feeder linkage configured to couple to the cart and to apply a force to advance or retract the cart along at least a portion of the inner shaft, and an applicator configured to mount the cart to the inner shaft.

An example method using the example effector deployment system includes disposing a concentric cylinder system proximate to a localized target zone of tissue forming a lumen of a body, such that the localized target zone is between a distal tip of an outer cylinder and a distal tip of an inner cylinder of the concentric cylinder system, and using an applicator to mount an effector deployment system to a portion of the inner shaft. The effector deployment system includes a cart to configured to slidably couple to the applicator and the inner shaft, a feeder linkage coupled to a proximal portion of the cart, and an effector component coupled to the cart and configured to perform a procedure on a portion of tissue. The method further includes using the feeder linkage to apply a force to advance or retract the cart along at least a portion of the inner shaft in a region of the localized target zone.

Example systems, methods, and apparatus herein provide an effector deployment system that includes a bus slidably attached to an inner shaft of a concentric cylinder system, an effector component configured to perform a procedure on a portion of tissue in a localized target zone, the localized target zone being between a distal tip of an outer cylinder and a distal tip of an inner cylinder of the concentric cylinder system, a feeder linkage configured to apply a force to advance or retract the bus along at least a portion of the inner shaft, a socket means configured to couple the feeder linkage to the bus, and a socket applicator configured to effect the coupling using the socket means.

An example method using the example effector deployment system includes disposing a concentric cylinder system proximate to a localized target zone of tissue forming a lumen of a body, such that the localized target zone is between a distal tip of an outer cylinder and a distal tip of an inner cylinder of the concentric cylinder system, and using a socket applicator to couple a feeder linkage of an effector deployment system to a bus using a socket means. The effector deployment system also includes an effector component. The bus is slidably attached to an inner shaft of a concentric cylinder system, the socket means couples the feeder linkage to a proximal portion of the bus, and the effector component is configured to perform a procedure on a portion of tissue. The method further includes using the feeder linkage to apply a force to advance or retract the bus along at least a portion of the inner shaft in a region of the localized target zone.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

One of ordinary skill in the art will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 3A-3C show another example effector deployment system, according to principles of the present disclosure.

FIGS. 6A-6B show example mounting elements configured as carts, according to principles of the present disclosure.

FIGS. 7A-7D show example socket means, according to principles of the present disclosure.

FIGS. 8A-8D show other example effector deployment systems, according to principles of the present disclosure.

FIGS. 10A-10B show an example of coupling of a cart to an applicator, according to principles of the present disclosure.

DETAILED DESCRIPTION

Figure 1A:
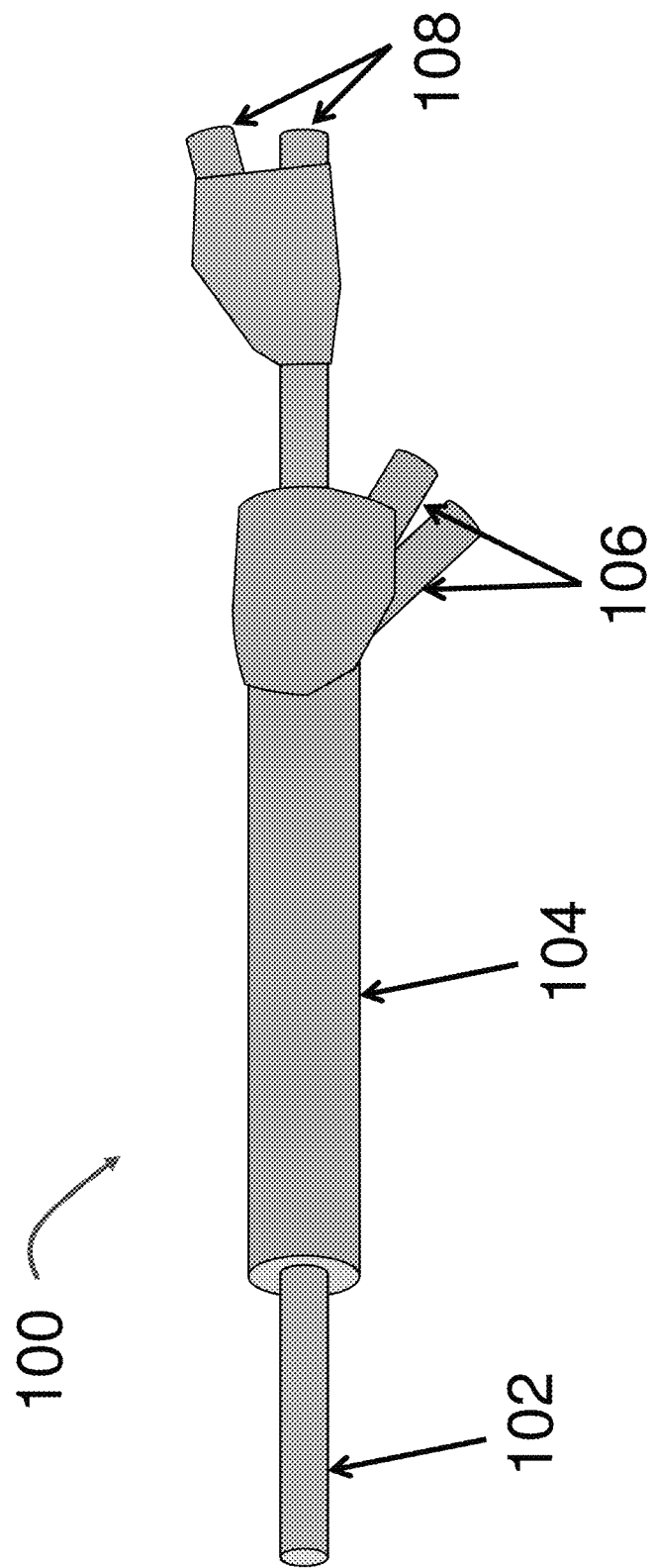
FIGS. 1A-1C show example concentric cylinder systems, according to principles of the present disclosure.

Following below are more detailed descriptions of various concepts related to, and embodiments of, systems, devices, apparatus and methods that allow for coupling of an effector deployment system as an adjunctive to a concentric cylinder system. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

With respect to surfaces described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a surface or layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the surface, and each other.

The terms "disposed on" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

As used herein, the term "proximal" refers to a direction towards a portion of a concentric cylinder system, or other instrument that a user would operate, such as but not limited to a grip or other handle. As used herein, the term "distal" refers to a direction away from the grip or other handle of the concentric cylinder system, or other instrument.

During certain procedures using many concentric cylinder systems, attempt is made to localize a vascular region in order to allow that region to be treated while minimizing systemic side effects. Non-limiting examples of concentric cylinder systems are described in connection with FIGS. 1A 1C hereinbelow. One class of such concentric cylinder systems uses an occlusive balloon mounted on the distal portion of the inner shaft, a non-limiting example of which is described in connection with FIG. 1B. The occlusive balloon isolation system can be used to demark the region distal to the balloon from the region proximal to the isolation balloon to define a target zone of a tissue lumen (also referred to herein as a demarked zone or a "to-be-treated" zone). A tissue lumen herein can be any orifice, passageway, hollow, or other opening existing or formed in tissue. Another class of such concentric cylinder systems is a dual-balloon concentric cylinder system, a non-limiting example of which is described in connection with FIG. 1C. Other non-limiting examples of concentric cylinder systems are disclosed in, e.g., U.S. Pat. Nos. 8,721,592, 8,900,185, and 9,028,442. The example adjunctive devices herein are also applicable to infusion catheters, such as but not limited to the system disclosed in U.S. Pat. Nos. 8,062,251 and 8,251,948. In various examples, a target zone may be defined as a controlled zone or other specified location established at a location in the vasculature relative to the tissue lumen, or may be a portion of the tissue lumen that is demarked (including being fully isolated or partly isolated) by isolation balloons or other occlusive component.

While the example systems herein are described relative to a concentric cylinder system, they can be applicable to other types of intravascular systems that can be used to target a localized vascular region, including other examples described herein.

The effector deployment systems described herein are adjunctive to the concentric cylinder systems, to perform additional or supplemental procedures on a target zone of the tissue lumen.

FIG. 1A illustrates a non-limiting example concentric cylinder system 100. Example concentric cylinder system 100 includes an inner shaft 102, an outer shaft 104 that includes one or more lumens, connectors 106 to the one or more lumens of the outer shaft 104, and connectors 108 to the one or more lumens of the inner shaft 102. The proximal portion 109 of the inner shaft also can include one or more lumens. The outer cylinder 104 of the example concentric cylinder system 100 defines the proximal edge of the target zone of a tissue lumen, while the inner shaft 102 extends beyond the outer cylinder 104 and defines the distal end of the target zone.

Figure 1B:
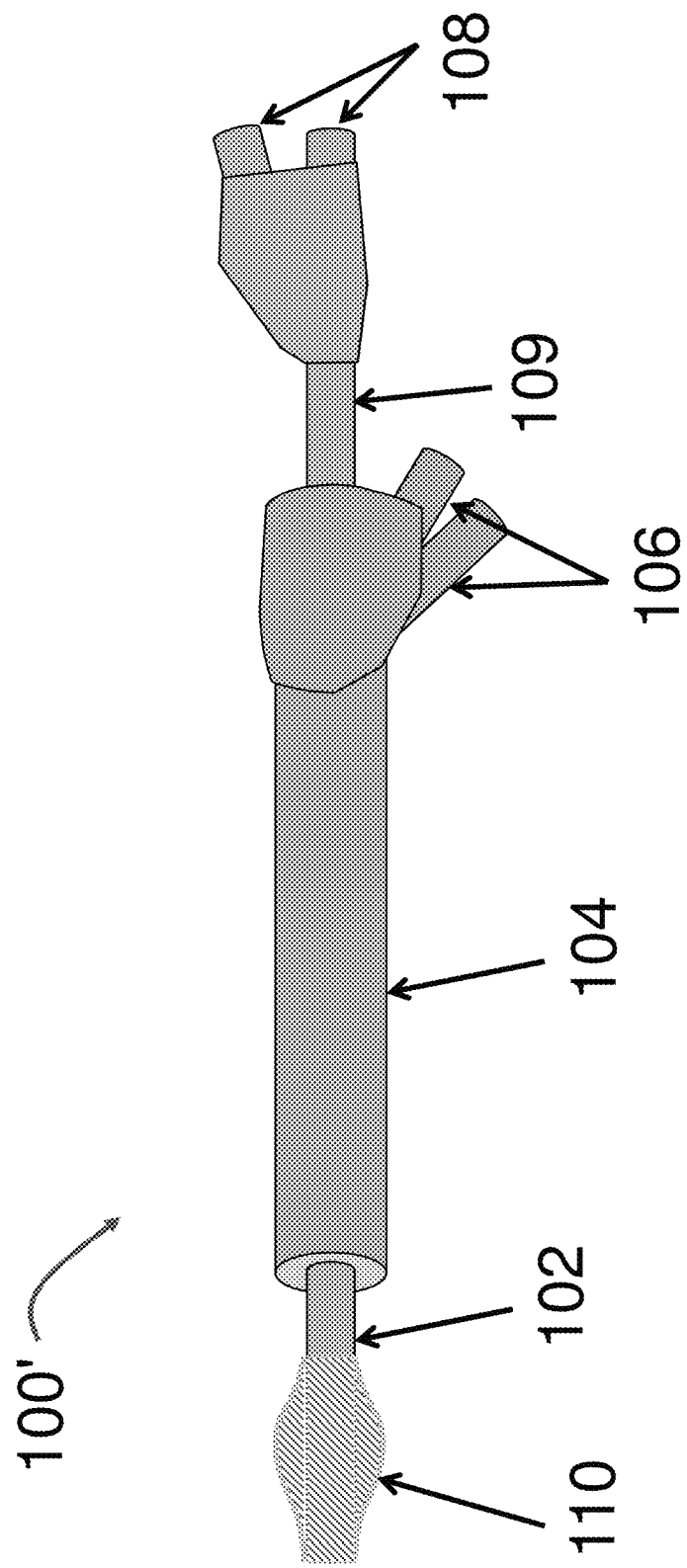

As shown in the non-limiting example of FIG. 1B, the concentric cylinder system 100' may also include a deployable or expandable component 110 disposed at the distal end of the inner shaft 102. In this example, the deployable or expandable component 110 is illustrated as an isolation balloon. In other examples, the deployable or expandable component 110 can be any other technology in the art that may be used to demark the target zone of the tissue lumen, such as but not limited to a deployable netting, or any other component that can be used to reduce or impede fluid flow at the distal end of the concentric cylinder system 100'.

Figure 1C:
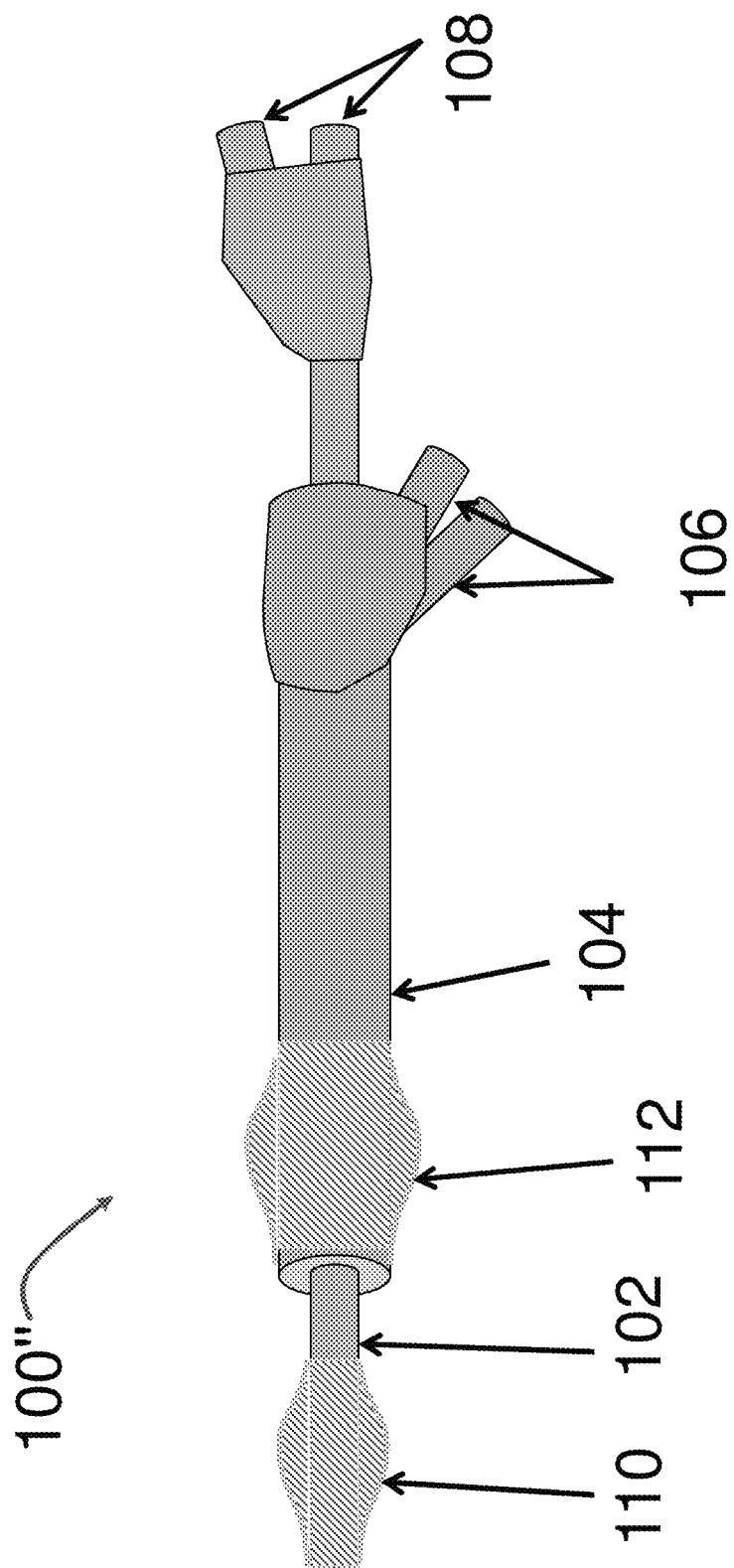

As shown in the non-limiting example of FIG. 1C, the concentric cylinder system 100" may also include a first deployable or expandable component 110 disposed proximate to the distal end of the inner shaft 102 and a second first deployable or expandable component 112 disposed proximate to the distal end of the outer shaft 104. The first deployable or expandable component 110, or second deployable or expandable component 112, or both, can be any other technology in the art that may be used to demark the target zone of the tissue lumen, such as but not limited to an isolation balloon, a depoyable netting, or any other component that can be used to reduce or impede fluid flow.

The present disclosure provides example effector deployment systems that are adjunctive to the concentric cylinder system. As described hereinbelow, the example effector deployment systems include a mounting element that allows them to follow a shaft. For example, the mounting element can be caused to follow a guidewire or other shaft of a distal balloon inside a proximal shaft of a concentric cylinder system. An example mounting element allows an adjunctive device herein to be combined in operation to a concentric cylinder system. An example adjunctive device herein can include an effector component that can be used to modify or improve the desired procedure or other operations in a controlled target zone of the tissue lumen. The example effector deployment systems allow an operator using an occlusive balloon isolation system, or a concentric-cylinder system, or other similar system, to apply an effector component to effect a diagnostic procedure and/or a treatment procedure in a portion of the tissue lumen demarked as the target zone. In different examples, the effector component provides additional capabilities that allows for modification, improvement, and/or complementing of a treatment procedure being applied in the demarked target zone.

Figure 2A:
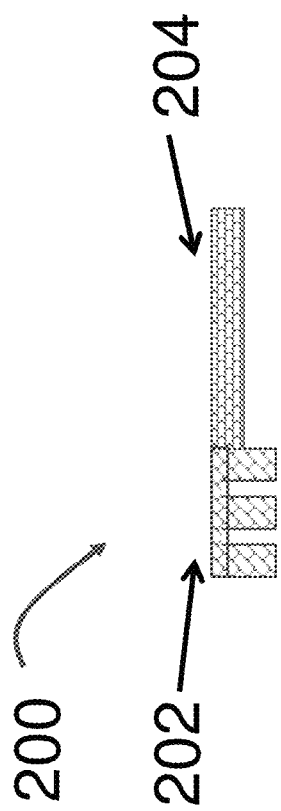
FIGS. 2A-2B show an example effector deployment system, according to principles of the present disclosure.

FIG. 2A illustrates an example effector deployment system 200 that includes a mounting element 202 and at least one effector component 204.

Figure 2B:
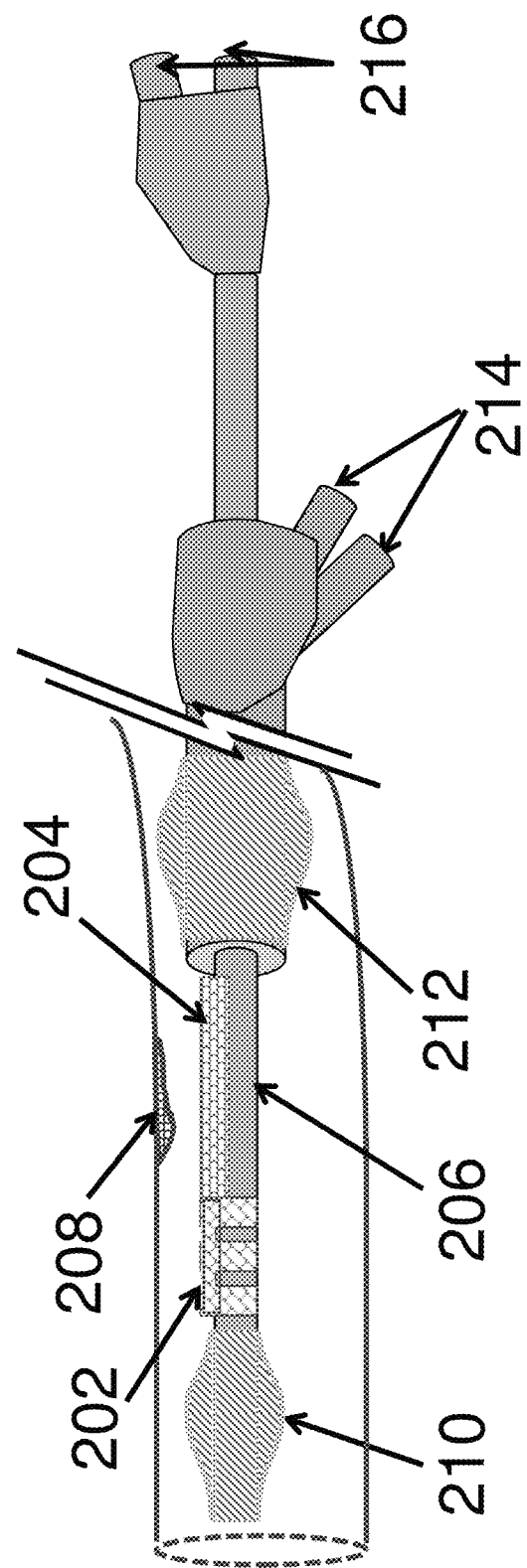

FIG. 2B shows the example effector deployment system 200 coupled to an example concentric cylinder system. As shown in the example of FIG. 2B, the mounting element 202 and effector component 204 of the example effector deployment system 200 can be coupled to the portion of the inner shaft 206 of the concentric cylinder system disposed proximate to a targeted region 208 of a tissue lumen. The overall target zone of the tissue lumen is demarked between isolation balloons 210 and 212. Connectors 214 to the one or more lumens of an outer shaft (not shown), and/or connectors 216 to the one or more lumens of the inner shaft 206, can be used for performing procedures in the tissue lumen.

As a non-limiting example, the effector component can be any component or subsystem that can be implemented to perform a diagnostic or treatment procedure, or any other useful action, in the target zone of the tissue lumen. In various example effector deployment systems, the effector component may be an "active" component or a "passive" component. As defined herein, a passive effector component can be deployed or otherwise operated in the target zone using little more than the force or energy required to dispose the effector deployment system at the target zone of the tissue lumen. By contrast, an active effector component requires some amount of additional force or energy to deploy or otherwise operate when the effector deployment system reaches the target zone, beyond the forces and linkage required to move effector deployment system in and out of the target zone.

Non-limiting examples of a passive effector component include a spiral, a mesh or a network of wire effector component, a stirring means, a coil, a blade, a loop, or a drug or pharmaceutical delivery formulation. The drug or pharmaceutical formulation can be a solid material formed as a bulk structure or a thin-film at a portion of the passive effector component. The drug or pharmaceutical formulation can be disposed at a portion of the passive effector component that allow for dissolution of the formulation to release active agents once the passive effector component is in the target zone of the tissue. The example passive effector component can be formed of a plastic, or a metal, or other material. A spiral effector component could be moved forward and backward in the target zone to stir a liquid in the target zone (i.e., to serve as a stirring means), thereby improving the mixing of materials in the target zone. A stirring means can be a benefit in the case where the target zone includes a thrombus and the concentric cylinder system is used to apply a thrombolytic agent, such as but not limited to a urokinase, to the target zone. In that case, the stirring of the thrombus and the thrombolytic agent could improve their mixing and help to increase the rate or efficiency of thrombus dissolution by the thrombolytic agent. The example mesh or network of wire effector component could be advanced into a thrombus for an appropriate period of time to cause it to set in the thrombus. On withdrawal, the passive effector component would carry or drag all or parts of the thrombus out of the target zone, thereby performing a passive thrombectomy procedure.

Non-limiting examples of active effector components include an inflatable balloon or shaped inflatable device, a deployable member (including a netting or a mesh), an agent delivery module, an optical component, an ultrasonic component, an electric component, a magnetic component, a fluidic component, a pneumatic component, a chemical component, a mechanical component, a drug or pharmaceutical delivery lumen, or other similar means of interacting with the tissue lumen at the target zone. In an example, a pump, syringe, or other component can be used to introduce a liquid, gel, or other drug or pharmaceutical formulation through the delivery lumen.

In an example, an inflatable balloon may also serve as a stirring means or an active thrombectomy means. An example delivery module can be configured as a plastic tube with a closed end, including side ports over its distal region, and an internal lumen arranged so that a drug or other mixture including an active agent could be injected from the proximal end of lumen and flow out to a desired region of the target zone.

FIG. 3A illustrates another example effector deployment system 300 that includes a mounting element 302 coupled at or near the distal end of a feeder linkage 305.

FIG. 3B shows the example effector deployment system 300 coupled to an example concentric cylinder system. As shown in the example of FIG. 3B, the mounting element 302 can be disposed at a proximal part of inner shaft 306 of the example concentric cylinder system. The feeder linkage 305 is configured to allow an operator to move the mounting element 302 along the inner shaft 306, to advance it to or retract it from the proximity of a targeted region 308 of the target zone of tissue lumen. The overall target zone of the tissue lumen is demarked between isolation balloons 310 and 312. Connectors 314 to the one or more lumens of an outer shaft (not shown), and/or connectors 316 to the one or more lumens of the inner shaft 306, can be used for performing procedures in the tissue lumen.

Figure 3C:
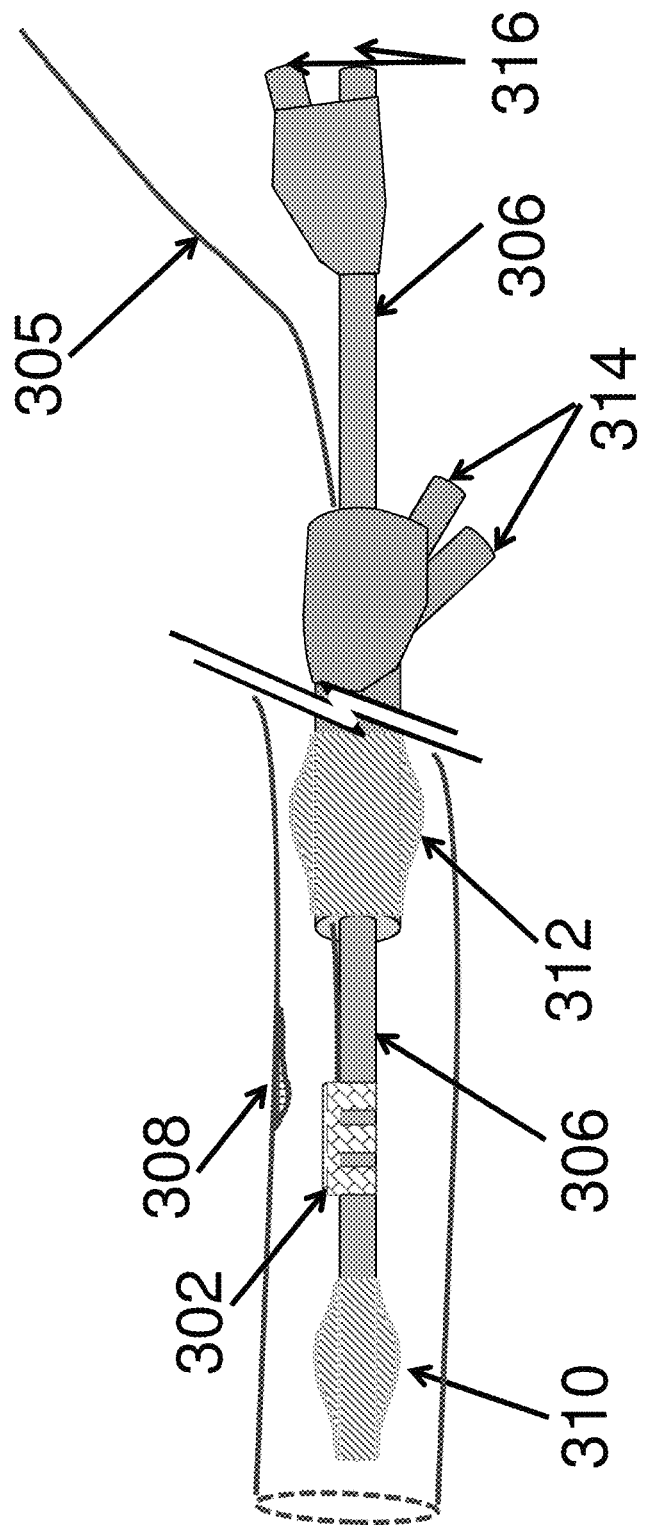

FIG. 3C shows the example effector deployment system 300, as a result of the feeder linkage 305 being used to advance the mounting element 302 from the proximal part of inner shaft 306 to a distal portion of the example concentric cylinder system, positioned in the target zone.

Figure 4A:
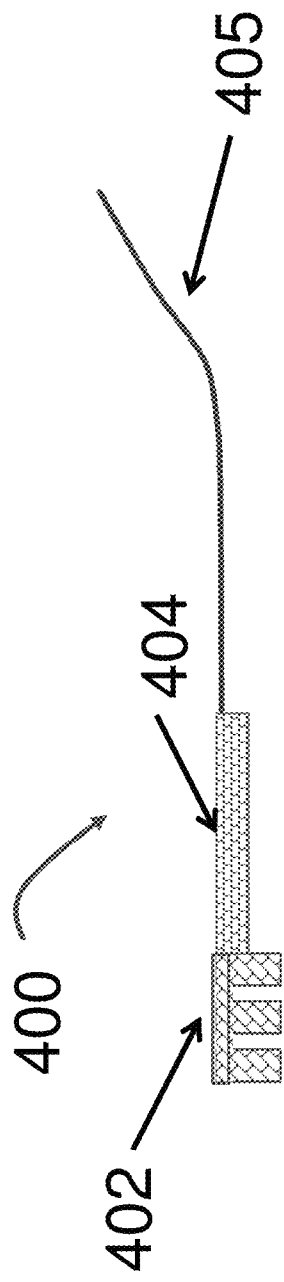
FIGS. 4A-4B show another example effector deployment system, according to principles of the present disclosure.

FIG. 4A illustrates another example effector deployment system 400 that includes a mounting element 402 and an effector component 404 coupled at or near the distal end of the feeder linkage 405.

Figure 4B:
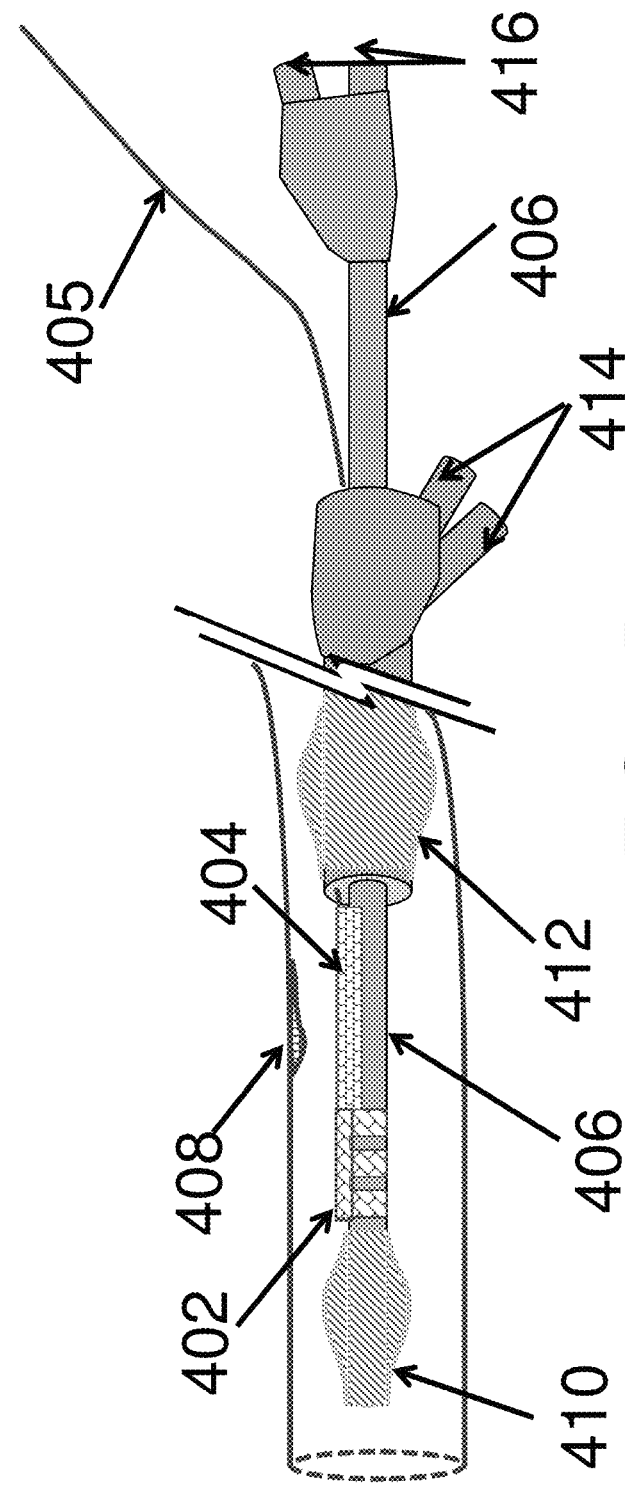

FIG. 4B shows the example effector deployment system 400 coupled to an example concentric cylinder system. The mounting element 402 and an effector component 404 are shown coupled to a distal part of inner shaft 406. The feeder linkage 405 allows an operator to move the mounting element 402 and the effector component 404 along the inner shaft 406, to advance it to or retract it from the proximity of a targeted region 408 of the target zone of tissue lumen. The overall target zone of the tissue lumen is demarked between isolation balloons 410 and 412. Connectors 414 to the one or more lumens of an outer shaft (not shown), and/or connectors 416 to the one or more lumens of the inner shaft 406, can be used for performing procedures in the tissue lumen.

In an example effector deployment system, a passive effector component can be deployed, or otherwise effected in the target zone using little or no more than the force or energy required to dispose the effector deployment system at the target zone of the tissue lumen, including through use of the shaft of the concentric cylinder system or the feeder linkage. An active effector component can require some amount of additional force or energy to deploy or otherwise operate when the effector deployment system reaches the target zone. The example effector deployment system further includes at least one additional control connector component to supply the additional force or energy to the active effector component.

In an example effector deployment system, the one or more control connector components can be coupled to the active effector component, to actuate the effector component. For example, the control connector component can be an integral component of the feeder linkage, can be a second component coupled to the feeder linkage, or can be a separate component from the feeder linkage, such as but not limited to a second or third linkage. For example, a second or third mechanical linkage can be actuated to deploy needles or other components to dispose them to a desired position relative to the tissue lumen. The one or more control connector components can be used to apply force in the same direction or in an opposite direction to the feeder linkage. For example, once a feeder linkage is used to push a mounting element towards the target zone, the one or more control connector components can be effected in the opposite direction to cause a sleeve of the effector component to retract to deploy the needles or other components.

In an example, the one or more control connector components can be coupled to a computing device. One or more processing units of the computing device be programmed to execute processor executable instructions to cause the one or more control connector components to actuate the effector component. As non-limiting example, based on execution of the processor executable instructions, the one or more control connector components can be caused to actuate the effector component using a change in the temperature, application of an electrical pulse, application of an optical excitation, generation of an ultrasonic impulse, pump a drug or pharmaceutical formulation through a lumen, or other means of activation or actuation.

In any example herein, including in connection with any of FIG. 3A, 3B, 3C, 4A or 4B, the feeder linkage can serve multiple purposes. In an example, the feeder linkage 405 serves to hold the effector component 404 and allow force to be applied to advance the effector component 404 into or out of the target zone, or to retract the mounting element 402 from the target zone to the proximal part of the inner shaft 406. The feeder linkage 405 also couples to the effector component 404 at or near its distal end. In various examples, the feeder linkage 405 can be a stiff wire, rhombus or scissor linkages, a telescoping line, or other series of rigid or semi-rigid links.

In an example where the example effector deployment system includes an active effector component, the feeder linkage can include additional structure or features to provide the additional energy or force required to activate or actuate the active effector component, and/or the agent to be dispensed by the active effector component. Examples of such additional structure or feature include a lumen, an additional mechanical wire, an optical fiber, an electrical wire, a fluid line, a hydraulic line, a pneumatic line, a control arm, or other activation means. In a non-limiting example, the feeder linkage can include a shaft with a balloon inflation lumen, for advancing and retracting the active effector component. In another non-limiting example, the feeder linkage can include an additional wire for pushing and pulling a flexible shaft including a balloon inflation lumen. In any example herein, the feeder linkage can include one or more active means to provide support and actuation to an active effector component, which may be implemented at a distal portion of the concentric cylinder system via a distal connection.

Figure 5:
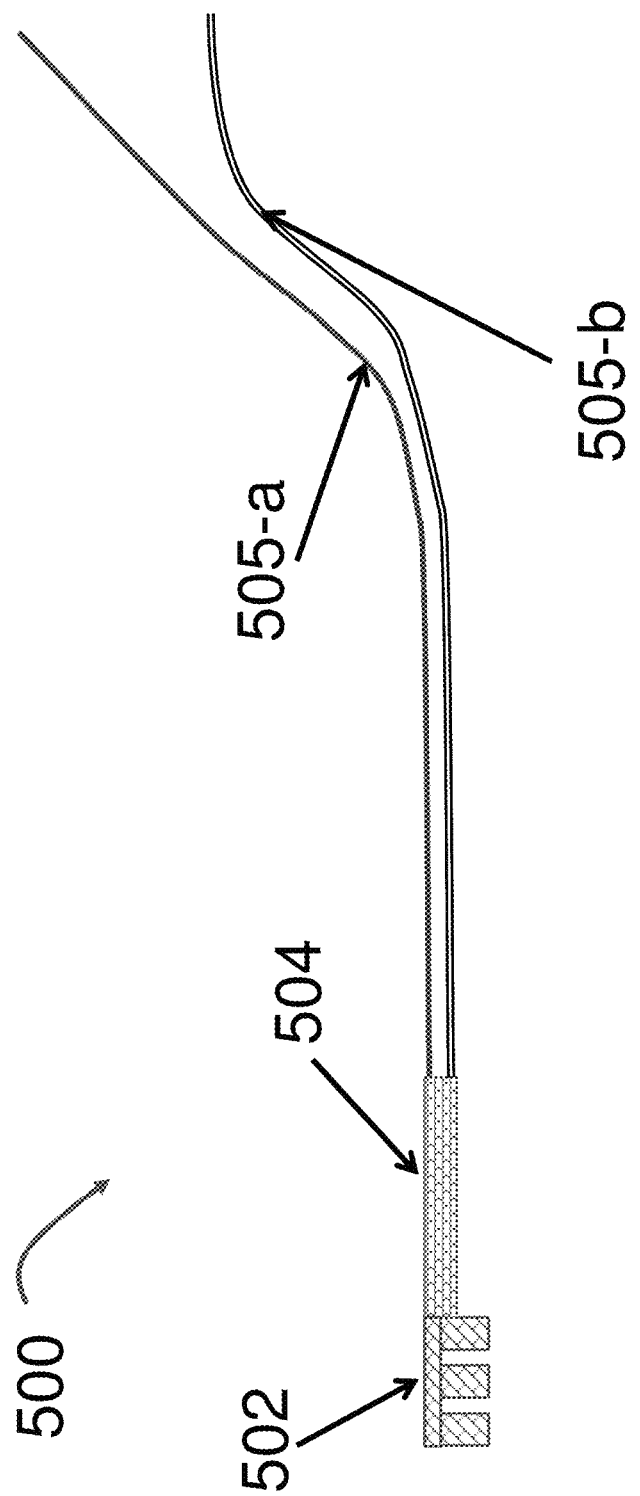
FIG. 5 shows another example effector deployment system, according to principles of the present disclosure.

FIG. 5 shows a non-limiting example effector deployment system 500 that includes a mounting element 502 and an effector component 504 coupled to the distal end of a dual-element feeder linkage 505-a, 505-b. In this example, the feeder linkage element 505-a can be used to advance and retract the mounting element 502 and effector component 504 along a shaft, and feeder linkage element 505-b can be used as an active means to provide active control and/or fluid access to the effector component 504. In non-limiting examples, feeder linkage element 505-b can include a lumen, an additional mechanical wire, an optical fiber, an electrical wire, a fluid line, a hydraulic line, a pneumatic line, a control arm, or other activation means.

In any example herein, including in connection with any of FIG. 2A, 2B, 3A, 3B, 3C, 4A or 4B, the mounting element is either configured to be removable from the inner shaft (referred to herein as a "cart") or non-removable from the inner shaft (referred to herein as a "bus").

In any example herein, the inner surface of the mounting element can be formed from, or at least partially covered with, a material that enables proper functioning of the mounting element. For example, the material preferably provides a sufficient amount of friction against the shaft of the concentric cylinder system to allow displacement of the mounting element along the shaft, but also cause the mounting element to apply a sufficiently strong grip of the shaft during use of the effector component.

FIG. 6A shows an example of a mounting element configured as a cart 602. The example cart 602 includes one or more circling elements 603 (such as but not limited to prongs) that surround a shaft 604 as a means of attachment to a concentric cylinder system. For clarity, as portion of the shaft 604 is shown using dashed lines. The example circling elements 603 allow the cart 602 to remain mounted to the shaft while the cart 602 is slid or pushed along the shaft 604 into and out of a target zone of the tissue lumen, and to be removed from the shaft when desired. Given that the example cart 602 is removable, the cart 602 can be coupled to a distal portion of the inner shaft of a concentric cylinder system while the proximal portion of the inner shaft is in place in the tissue lumen, advanced into and withdrawn from the target zone, and also removed from the shaft without the need to remove the concentric cylinder system from the tissue lumen. In an example effector deployment system, the cart 602 can be mounted to the distal end of the feeder linkage.

FIG. 6B shows another example of a mounting element configured as a cart 622. The example cart 622 includes circling elements 623-a, 623-b (such as but not limited to prongs) that surround a shaft 624 as a means of attachment to a concentric cylinder system. For clarity, as portion of the shaft 624 is shown using dashed lines. The example circling elements 623-a, 623-b allow the cart 622 to remain mounted to the shaft while the cart 622 is slid or pushed along the shaft 624 into and out of a target zone of the tissue lumen, and to be removed from the shaft when desired. Similarly to the example of FIG. 6A, the cart 622 can be coupled to a distal portion of the inner shaft of a concentric cylinder system, while the proximal portion of the inner shaft is in place in the tissue lumen, advanced into and withdrawn from the target zone, and also removed from the shaft without the need to remove the concentric cylinder system from the tissue lumen. In an example effector deployment system, the cart 622 can be mounted to the distal end of the feeder linkage.

As shown in FIG. 6B, each of the circling elements 623-a, 623-b includes an opening sections 625-a, 625-b that allows the example cart 622 to be mounted to and removed from the shaft 624. As shown in the example of FIG. 6B, the opening section 625-a of circling element 623-a can be at a differing, rotated position as compared to opening section 625-b of circling element 623-b. This alternating alignment of the opening sections 625-a and 625-b can prevent inadvertent decoupling of the cart 622 from shaft 624 as forces are applied to cause the cart 622 to advance into or withdraw from the target zone, or to deploy or use any effector component in the target zone.

Figure 6C:
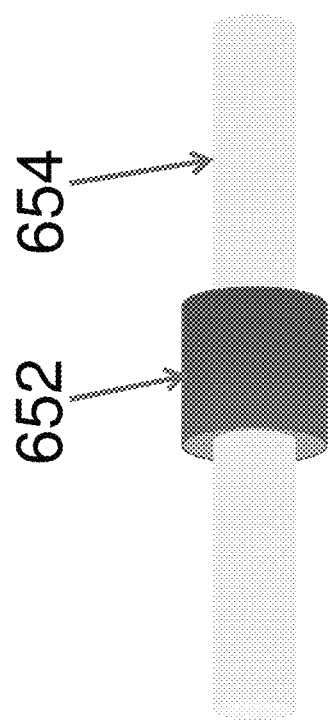
FIG. 6C shows an example mounting element configured as a bus, according to principles of the present disclosure.

FIG. 6C shows an example of a mounting element configured as a bus 652. The example bus 652 can be formed as a ring, a cylinder, or other conformation that can be maintained on the shaft 654 and slid or pushed along the shaft 654 to advance it into and withdraw it from the target zone of the tissue lumen. In an example effector deployment system, the bus 652 can be coupled to the distal end of the feeder linkage.

In any example herein, the feeder linkage may be coupled to the mounting element (i.e., the cart or bus) using one or more socket means. An example socket means can be formed as two or more socket units that combine through a coupling or mating mechanism to physically couple the feeder linkage to a portion of the cart or bus. The example socket units can be formed as a 'left' socket unit and a 'right' socket unit, or as a 'proximal' socket unit and a 'distal' socket unit, which mate together to form a binding connection. The socket means is configured such that forces (including forces to push or pull) can be transmitted the feeder linkage to the cart or bus across the socket units and the socket units do not disengage or otherwise separate. The coupling between the socket units can be engaged using a specified coupling procedure, and may be broken, or decoupled, by applying a specified decoupling procedure. The example socket means can be configured such that the coupling procedure and decoupling procedure would not be unintentionally triggered during the course of use of the example effector deployment system, including while being used to transmit the useful forces. In any example herein, the socket means can be any components that are configured to establish the specified functionality between the feeder linage and the cart or bus, and are configured to implement a variety of applicable coupling/decoupling procedures. For example, the socket means can be configured to transmit push or pull forces to slide a mounting element along an inner shaft from a proximal end of a concentric cylinder system to the target zone of the tissue lumen at the distal end of the concentric cylinder system. Non-limiting examples of coupling/decoupling procedures include twisting, threading, looping, rotating, magnetic coupling, electrostatic coupling, mechanical coupling (including hook-and-loop fasteners or touch fasteners), or controlled adhesive based chemical means of coupling and decoupling.

In any example herein, the socket means also may be configured to establish a desired functionality between the feeder linage and an active effector component, including transmittal of effector activation control where applicable.

The functionality of an example effector deployment system herein can be changed while the distal part of the concentric cylinder system is disposed in situ in a patient, without need to remove the concentric cylinder system from the patient and without need for threading a component on a guidewire.

In an example where the effector deployment system includes a cart, the socket means can be engaged to couple the feeder linkage to the cart prior to the cart being coupled to a proximal part of an inner shaft of the concentric cylinder system. To change the functionality of the effector deployment system, a different set of a feeder linkage and effector component may be swapped in and coupled to the same cart (or a different cart) via the socket means, prior to the cart being coupled to the inner shaft.

In any example where the effector deployment system includes a bus, the functionality of the effector deployment system can be changed while the distal part of the concentric cylinder system is disposed in situ in a patient. A different set of a feeder linkage and effector component can be swapped in and coupled to the bus via the socket means when the bus is positioned at a proximal part of the inner shaft.

Figure 7A:
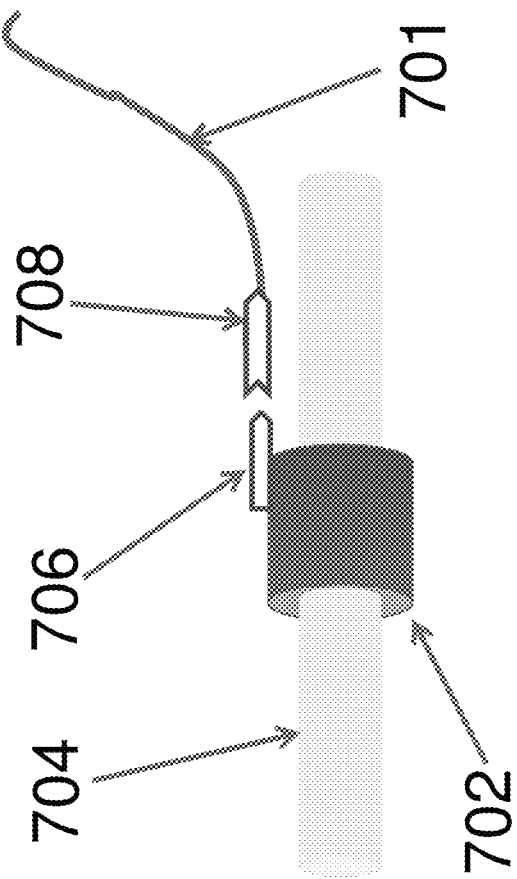
Figure 7C:
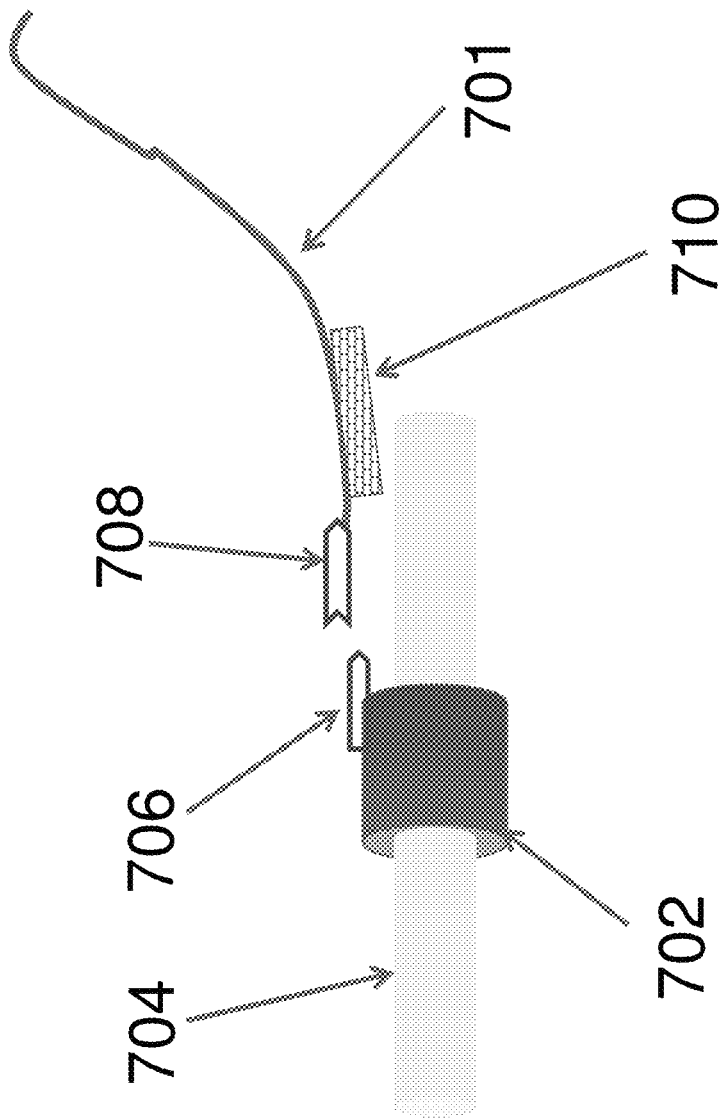

FIGS. 7A-7C show non-limiting example socket means that can be used to couple a feeder linkage 701 to a bus 702 mounted to a shaft 704.

The example socket means shown in FIG. 7A is formed from a distal socket unit 706 and a proximal socket unit 708. The proximal socket unit 708 can be coupled reversibly or irreversibly to the feeder linkage 701. The distal socket unit 706 can be coupled reversibly or irreversibly to the bus 702. The distal socket unit 706 of the example socket means is configured to couple with the proximal socket unit 708 of the example socket means. In some examples, the coupling and decoupling between the distal socket unit 706 and the proximal socket unit 708 can be engaged reversibly using any applicable coupling and decoupling procedures. In other examples, the socket means can be configured for irreversible attachment between the distal socket unit 706 and the proximal socket unit 708. In an example where the distal and proximal socket units irreversibly attach to each other, the distal socket unit 706 may be coupled reversibly to the bus 702.

In another example, the distal socket unit 706 and the proximal socket unit 708 can be coupled in a manner that requires destructively reversible removal. In an example implementation, the proximal socket unit 708 can a wire loop or other unit that is separable from the distal socket unit 706 only using a destructive means, e.g., by cutting or breaking. The distal socket unit 706 could be re-usable, e.g., using a different section of the cut or otherwise broken proximal socket unit 708, or using an entirely different proximal socket unit 708. In another example implementation, both the proximal socket unit 708 and the distal socket unit 706 are removable using an irreversible destructive means, e.g., by cutting or breaking both.

The example socket means shown in FIG. 7B is formed from a distal socket unit 706' and a proximal socket unit 708'. In this non-limiting example, the distal socket unit 706' is formed as a loop attachment, and the proximal socket unit 708' is formed as a hook attachment. The coupling and decoupling between the loop attachment (distal socket unit 706') and the hook attachment (proximal socket unit 708') can be engaged using any applicable coupling and decoupling technique.

As shown in the example of FIG. 7C, an effector component 710 may be coupled to the feeder linkage 701 behind the proximal socket unit 708, prior to coupling of the distal socket unit 706 to the proximal socket unit 708. In another example, the distal socket unit 706 and the proximal socket unit 708 may be used to couple the feeder linkage 701 to the bus 702, prior to the effector component 710 being mounted to the feeder linkage 701. In any example herein, the socket means also may be configured to maintain a desired functionality between the feeder linage 701 and the active effector component 710, including for transmittal of effector activation control.

Figure 7D:
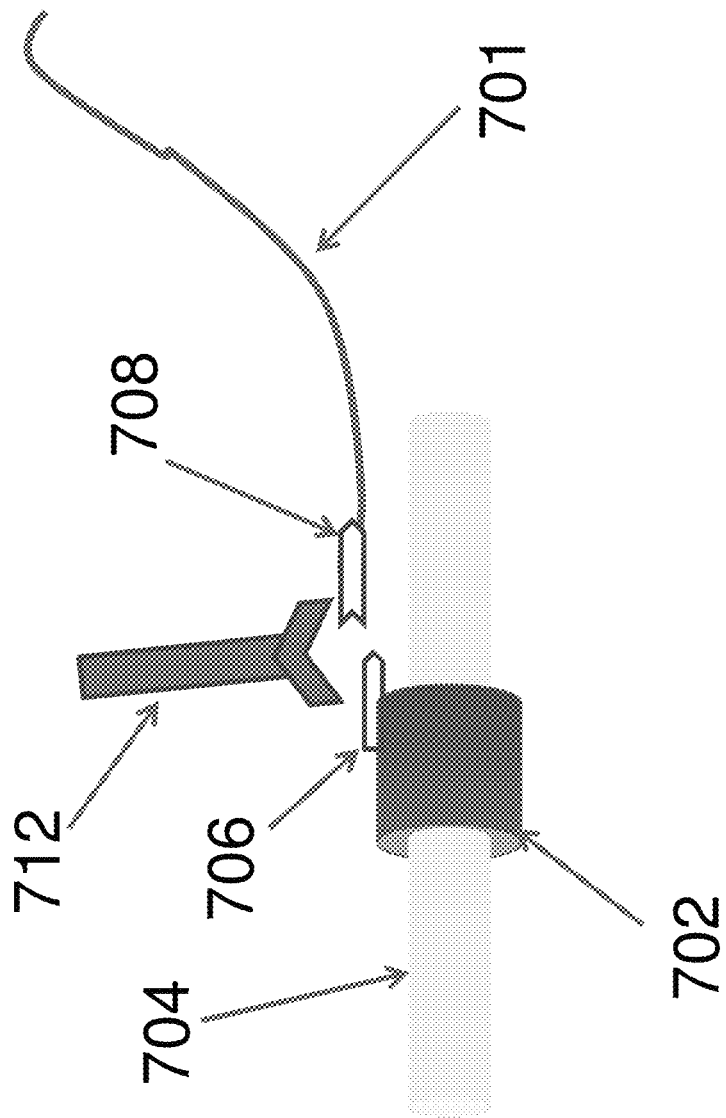

FIG. 7D shows a non-limiting example socket applicator 712 that can be used to attach or detach the socket units 706 and 708 of the socket means, for coupling the feeder linkage 701 to a bus 702 mounted to shaft 704. In operation, the socket applicator 712 can be used to reversibly or irreversibly couple the socket units 706 and 708. In an example, the socket applicator 712 can be used to couple the socket units 706 and 708 through thermal means, chemical means, electrochemical means, mechanical means, or any other applicable means.

Figure 8A:
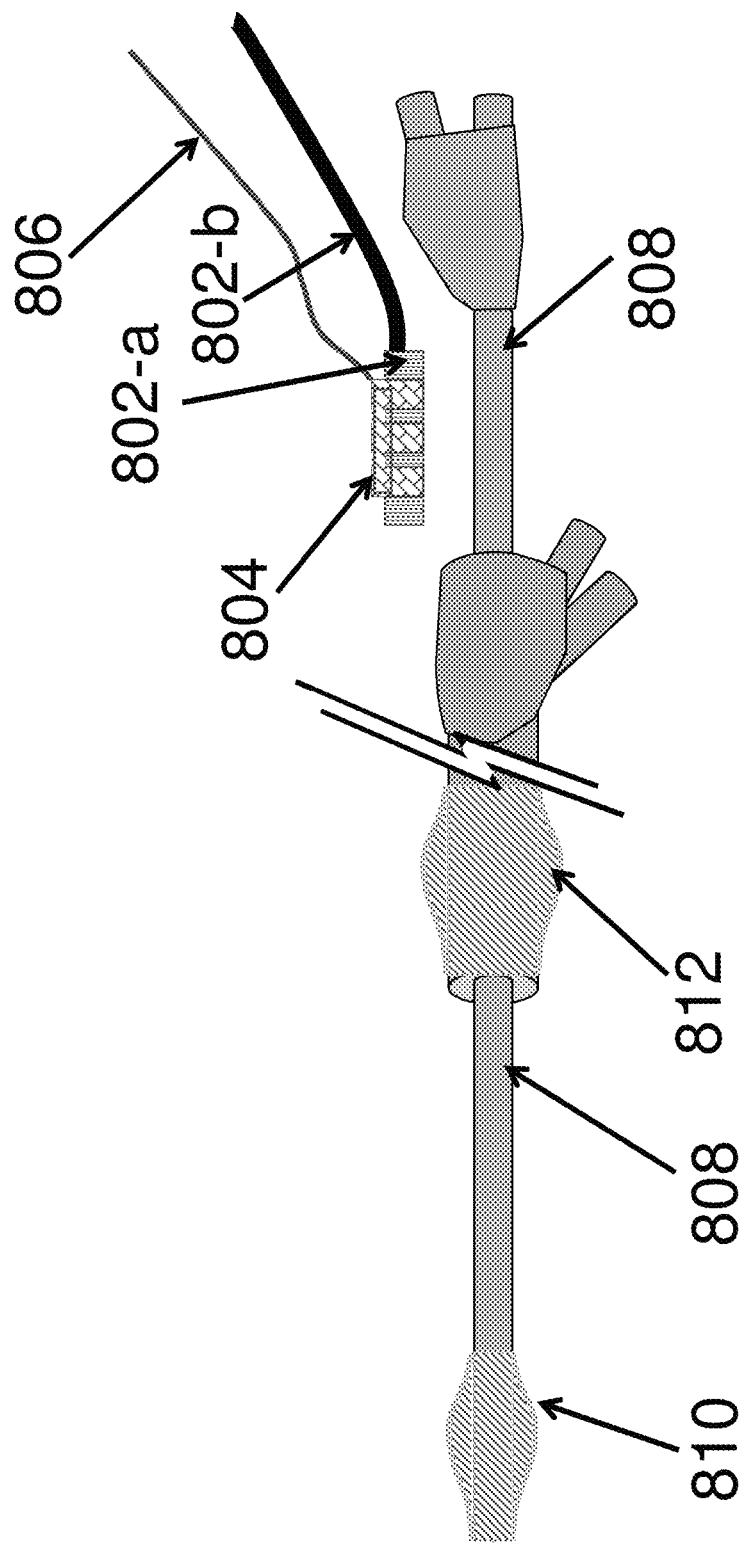
Figure 8B:
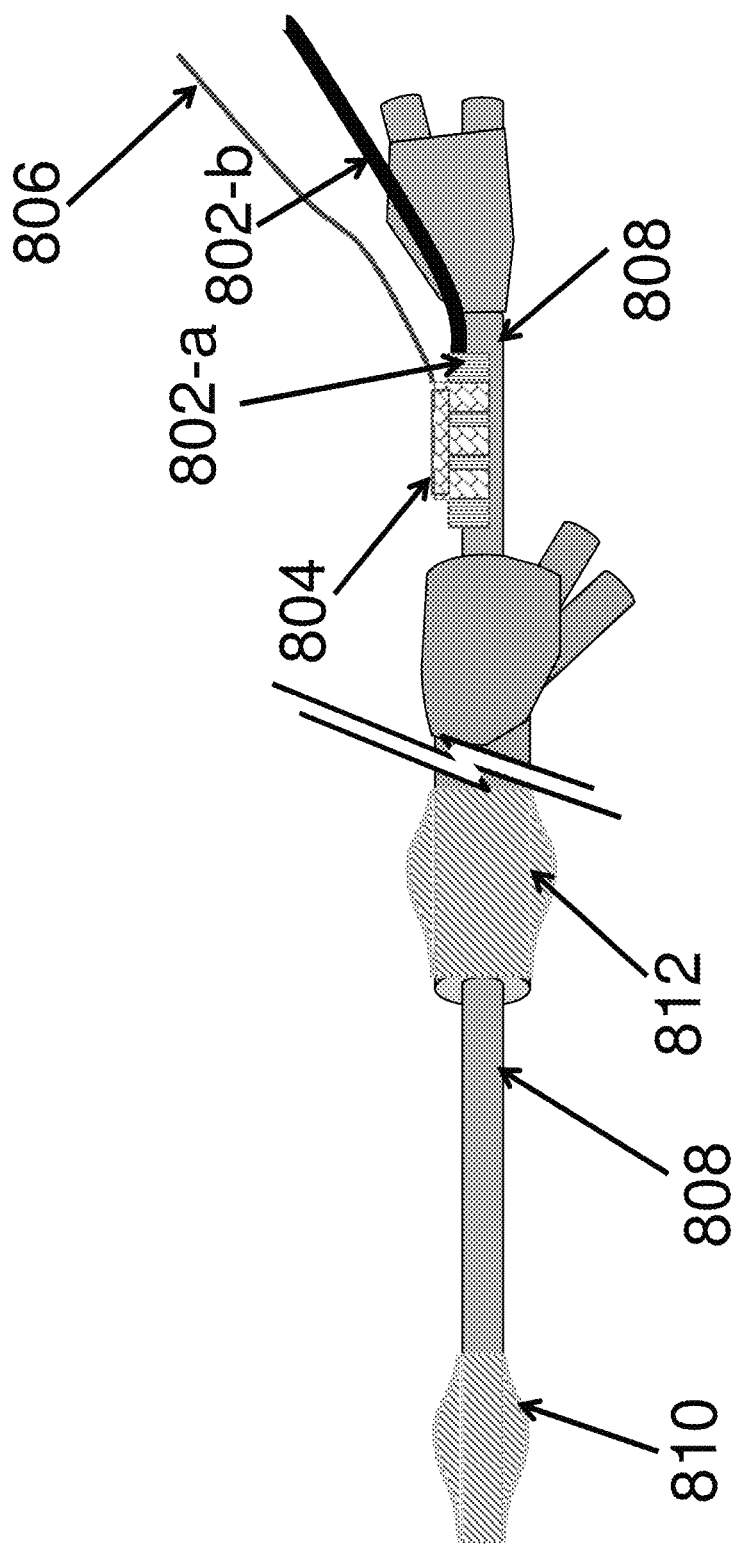

FIGS. 8A-8D show a non-limiting example effector deployment system that includes an applicator (having a coupling portion 802-*a* and a handle 802-*b*), a cart 804, and a feeder linkage 806. The coupling portion 802-*a* of the applicator is configured to mount the cart 804 to the proximal part of an inner shaft 808 of an example concentric cylinder system, such that the cart 804 grips the inner shaft 808 with sufficient force to remain in place during use. The handle 802-*b* can be configured to any shape that permits ease of application of the cart 804. As shown in FIG. 8A, the handle 802-*b* of the applicator can be used to bring the cart 804 in proximity to the proximal part of the inner shaft 808. As shown in FIG. 8B, the coupling portion 802-*a* of the applicator can be used to position the cart 804 on the inner shaft 808.

An example applicator herein can be used to open or hold open portions of the cart 804 so it may be more easily placed on the inner shaft 808. Upon withdrawal of the applicator, the cart 804 is coupled with a sufficiently firm hold to the inner shaft 808 so that it can be operated as describe herein. For example, the cart 804 can be pushed or pulled in the distal or proximal direction along the inner shaft 808 without decoupling under the loading forces of the intended use cases of the cart 804.

As shown in FIGS. 8C and 8D, the applicator is configured such that the cart 804 can be slid off the coupling portion 802-*a* onto proximal part of the inner shaft 808, leaving cart 804 mounted in place on the inner shaft 808.

Once the applicator is removed, the feeder linkage 806 can be used to advance the cart 804 from the proximal part of inner shaft 808 to a distal portion of the example concentric cylinder system, such as to within a target zone demarked between distal isolation balloon 810 and proximal isolation balloon 812 (shown in FIGS. 8A and 8B).

In an effector deployment system example according to FIGS. 8A-8D, an effector component may be coupled to the feeder linkage and/or to the cart 804 either prior to the applicator being used to couple the cart 804 to the inner shaft, or after the cart 804 is coupled to the inner shaft.

Figure 9B:
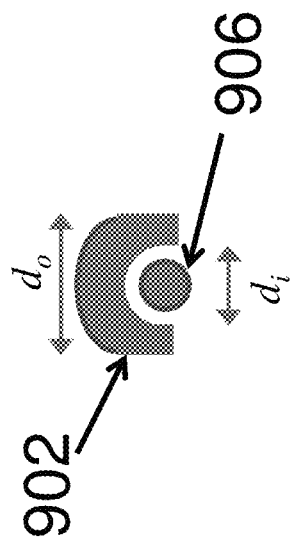
FIGS. 9A-9C show example applicators, according to principles of the present disclosure
Figure 9C:
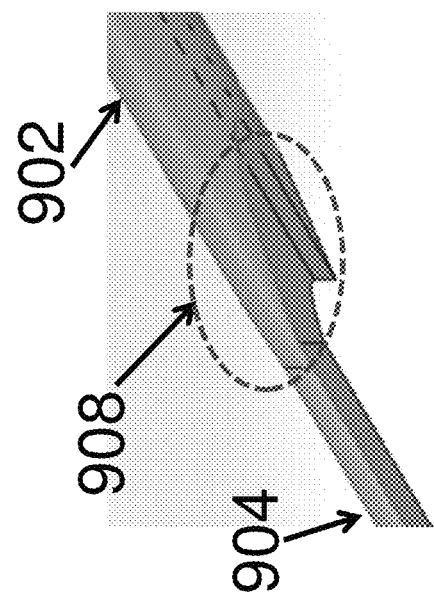
Figure 9A:
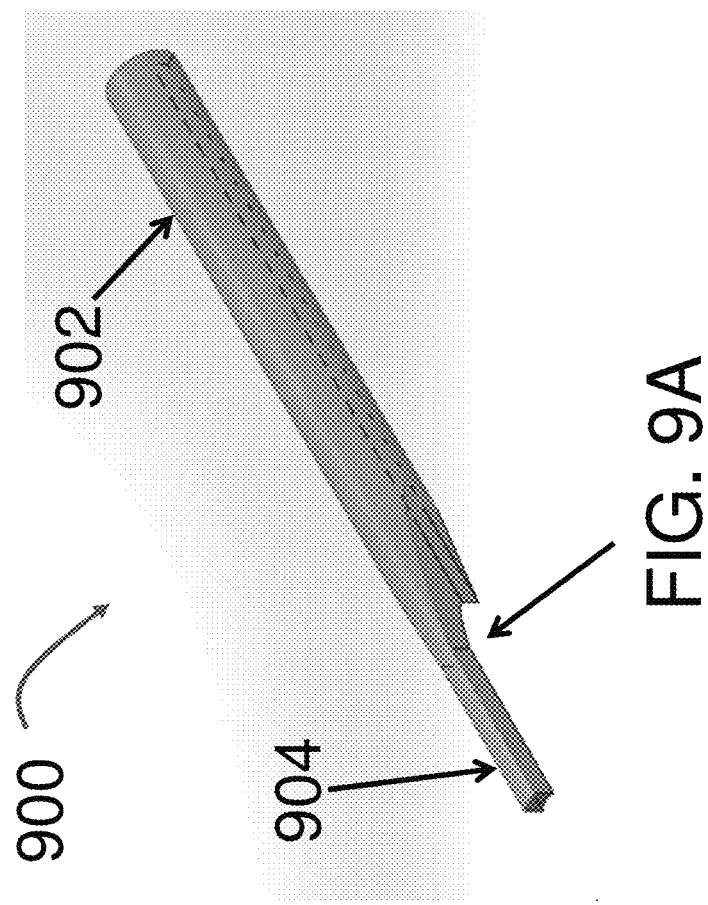

FIG. 9A shows a non-limiting example applicator 900 that can be used with an example cart described hereinabove. The example applicator 900 includes a coupling portion 902 that couples to the example cart, and an extension 904 that can be used to assist in the coupling of the cart to a shaft.

FIG. 9B shows a cross-section of the coupling portion 902 of an example applicator, as it is mounted on an example shaft 906 of a concentric cylinder system. The width ($d_i$) of the hollow inner portion of the coupling portion 902 approximates the diameter of the shaft 906. The outer dimension ($d_o$) of the coupling portion 902 can be made sufficiently wide to cause separation and spreading of the circling elements of the cart to assist with coupling the cart of the effector deployment system to the shaft of the concentric cylinder system. For example, the coupling portion 902 can be made to have an outer dimension ($d_o$) that causes the circling elements of the cart to separate and allow for easier coupling to the shaft of the concentric cylinder system. In an example, the outer dimension ($d_o$) of the applicator can be approximately the perimeter of the circling elements of the cart.

FIG. 9C shows a magnified image of the section 908 of the example applicator between the extension 904 and the coupling portion 902. In the example applicator of FIG. 9C, the lateral width increase gradually from the lateral dimension of the extension 904 to the outer dimension ($d_o$) of the coupling portion 902. For removal of an example cart that includes circling elements (such as but not limited to prongs or other separable coupling members), the gradually increasing width of section 908 of the applicator can be used for gradually separating the prongs (or other separable coupling members) from the shaft of a concentric cylinder system.

FIGS. 10A and 10B illustrate use of an example applicator (having a coupling portion 1002 and an extension 1004) to couple a cart 1006 from a shaft of an example concentric cylinder system. As shown in FIG. 10A, the extension 1004 is so dimensioned that it can be inserted between the circling elements of the cart 1006 and the shaft (not shown) of the example concentric cylinder system. As described in connection with FIG. 9C, the gradually increasing dimensions of the section between the coupling portion 1002 and the extension 1004 causes gradual separation of the circling elements (such as but not limited to prongs or other separable coupling members) of the cart 1006. As shown in FIG. 10B, the circling elements of the cart 1006 are substantially separated at the point that the cart 1006 is mounted on the coupling portion 1002 of the applicator. In operation, the procedure of FIGS. 10A and 10B can be performed to mount a cart 1006 to the coupling portion 1002 of an applicator. With the extension 1004 of the applicator positioned proximate to a shaft, the cart 1006 can be pushed from the coupling portion 1002 of the applicator towards the extension 1004. In this reverse direction, the gradually decreasing dimensions of the section between the coupling portion 1002 and the extension 1004 causes the circling elements (including prongs or other separable coupling members) of the cart 1006 to grip the shaft of the concentric cylinder system.

As shown in FIGS. 10A and 10B, an example applicator can also include one or more mounting features 1008, such as but not limited to flanges, segment, notches or other features, that the circling elements can be caused to rest on once the cart is coupled to the applicator.

As described hereinabove, example effector deployment systems according to the principles herein can include two or more of a mounting element, a feeder linkage, and an effector component. The example effector deployment system may be used to bring an effector means into the target zone established by a base concentric cylinder system, while at least a portion of that base concentric cylinder system is deployed in a patient. The example effector deployment system also may be configured for withdrawal of the mounting element and an effector component without removing the base concentric cylinder system. It will be apparent to one of ordinary skill in the art that, during any single procedure or multiple procedures, one or more effector deployment systems may be used to bring a sequence of similar or different effector components to the target zone, and implement the effector components as desired.

Figure 11A:
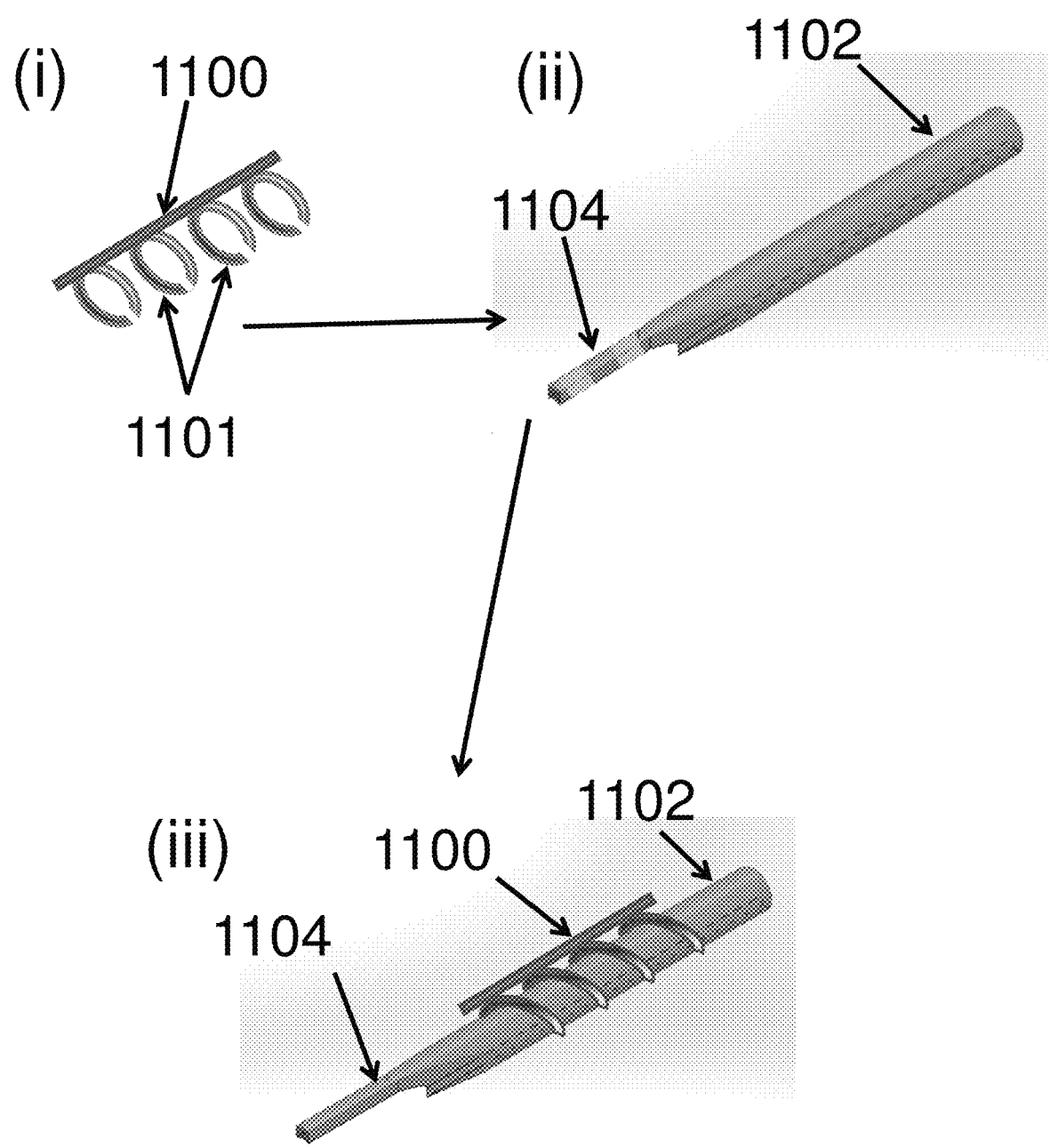
FIGS. 11A(i) through 11C(iv) show an example process flow for coupling an example effector deployment system to a concentric cylinder system, according to principles of the present disclosure.

FIGS. 11A(i) through 11C(iv) illustrate an example process flow for coupling an example effector deployment system to a shaft of a concentric cylinder system using an example applicator.

FIGS. 11A(i)-11A(iii) illustrate an example cart-applicator assembly procedure for mounting a cart 1100 to an applicator (having a coupling portion 1102 and an extension 1104). As shown in FIG. 11A(i), the cart 1100 includes a plurality of circling elements 1101. In the example cart-applicator assembly procedure, the extension 1104 of the application shown in FIG. 11A(ii) is inserted between the circling elements of the cart 1100. Similarly to as described in connection with FIG. 9C, the gradually increasing dimensions of the section of the applicator between the coupling portion 1102 and the extension 1104 causes gradual separation of the circling elements 1101 of the cart 1100 as the applicator is advanced through the circling elements 1101.

As also shown in FIG. 11A(iii), the circling elements 1101 of the cart 1100 are substantially separated at the point that the cart 1100 is mounted on the coupling portion 1102 of the applicator.

Figure 11B:
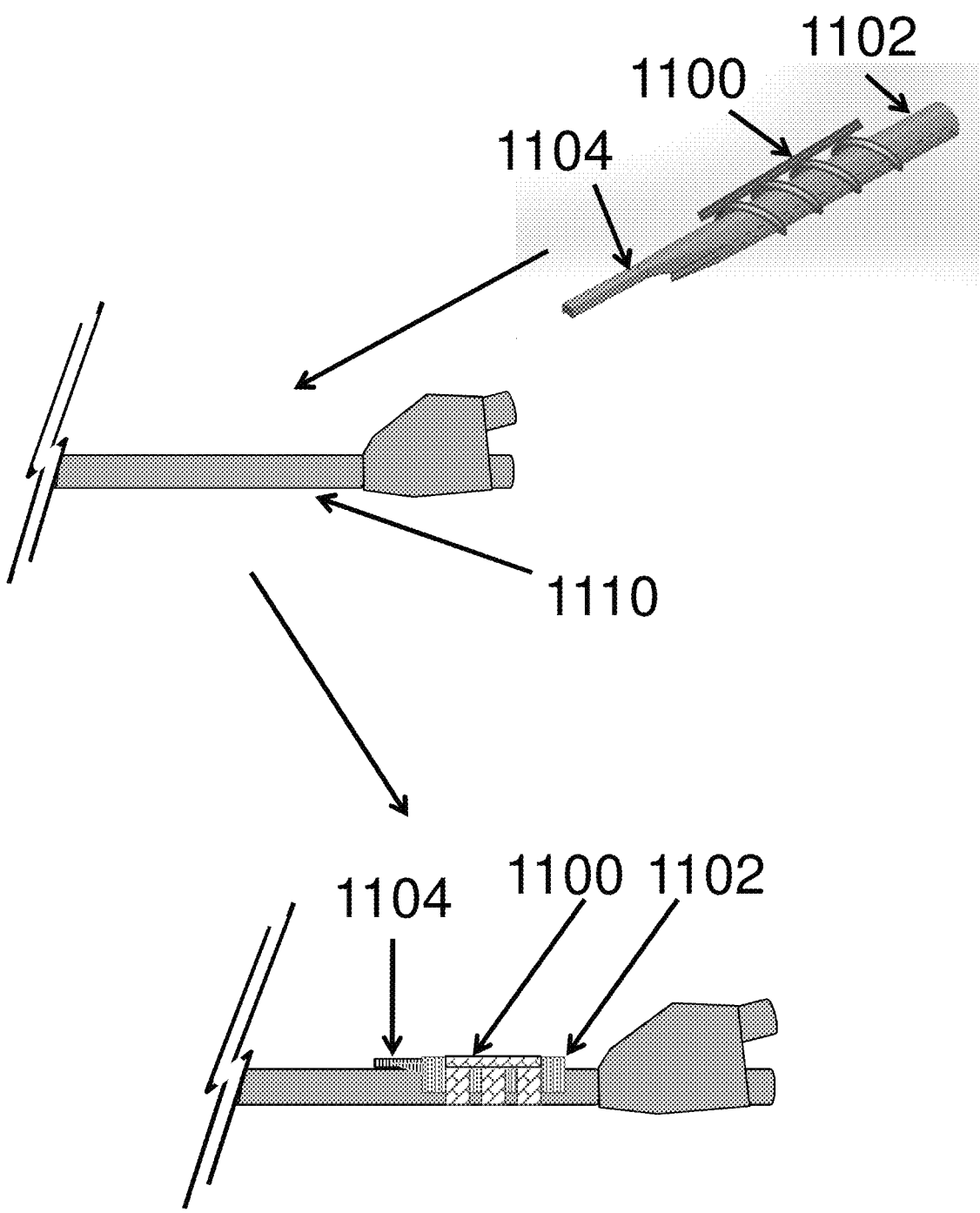

As shown in FIG. 11B, the example applicator with the cart 1100 mounted thereon can be disposed at a proximal portion of a shaft 1110 of a concentric cylinder system, such that the extension portion 1104 of the applicator is pointed towards the distal portion of the concentric cylinder system.

FIGS. 11C(i) 11C(iv) show an example cart disposition procedure, to couple the cart 1100 to the shaft 1110 of the example concentric cylinder system. FIG. 11C(ii) shows a cross-sectional view along line A-A' of FIG. 11C(i), showing the cart 1100 disposed on the distal portion 1102 of the applicator, with the applicator disposed on the shaft 1110 of the concentric cylinder system. As shown in FIG. 11C(i), with the extension 1104 of the applicator positioned proximate to the shaft 1110, the cart 1100 is pushed distally, and the applicator is pulled proximally, to move the circling elements 1101 from the coupling portion 1102 of the applicator towards the extension 1104. In this example, the gradually decreasing dimensions of the section between the coupling portion 1102 and the extension 1104 causes the circling elements 1101 of the cart 1100 to grip the shaft 1110 of the concentric cylinder system. FIG. 11C(iii) shows an intermediate stage in the procedure, where some of the circling members 1101 are gripping the shaft 1110, while others remain minted to the distal portion 1102 of the applicator. FIG. 11C(iv) shows a cross-sectional view along line B-B' of FIG. 11C(iii), showing the circling elements 1101 of the cart 1100 that are disposed on and gripping the shaft 1110 of the concentric cylinder system. With full withdrawal of the applicator, all of the circling elements 1101 of cart 1100 circle and grip the shaft 1110. In this manner, the applicator effects the coupling of the cart to the shaft of the concentric cylinder system.

In sum, the present disclosure provides example effector deployment systems configured with the capability of one or more effector components to be easily coupled to the inner shaft of a concentric cylinder system in such a manner that the effector component(s) may pushed along the inner shaft into the target zone. When the one or more effector components reach the target zone, the example effector deployment system provide an operator with the capability to interact with the tissue lumen in the target zone to perform a function modifying, improving, or complementing the treatment being applied by the base concentric cylinder system. In some examples, the example effector deployment systems include a complimentary applicator component for ease of application of some components of the example effector deployment system to the shaft of a concentric cylinder system.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention can be implemented in any of numerous ways. For example, some aspects of the implementations (such as the computer-controlled motor to aid the user-initiated mechanical manipulation) may be implemented using hardware, software or a combination thereof. When any aspect of an embodiment is implemented at least in part in software, the software code can be executed on any suitable processor or collection of processors, whether provided in a single computer or distributed among multiple computers.

The terms "program" or "software" are used herein in a generic sense to refer to any type of computer code or set of computer-executable instructions that can be employed to program a computer or other processor to implement various aspects of the present technology as discussed above.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A concentric cylinder effector deployment system comprising:
a concentric cylinder system comprising:
   an inner shaft having an inner shaft distal tip and a first deployable or expandable component positioned proximate to the inner shaft distal tip, and
   an outer shaft approximately concentric with and surrounding at least a portion of the inner shaft, and having an outer shaft distal tip and a second deployable or expandable component positioned proximate to the outer shaft distal tip; and
an effector deployment system configured to be attached to the concentric cylinder system and comprising:
   a mounting element configured to slidably couple to the inner shaft between the first deployable or expandable component and the second deployable or expandable component; and
   an effector component configured to couple to the mounting element at a proximal portion of the inner shaft and to perform a procedure on a portion of tissue proximate to a localized target zone that extends from the outer shaft distal tip to the inner shaft distal tip; and
   an applicator configured to mount and to remove the effector component to and from the inner shaft.

2. The system of claim 1, wherein the mounting element is a cart, wherein the cart comprises at least one circling element configured to surround a portion of the inner shaft and is removable from the inner shaft.

3. The system of claim 1, wherein the mounting element is a bus, and wherein the bus is attached to the inner shaft.

4. The system of claim 1, wherein the effector component is a passive component comprising one or more of a spiral, a mesh or a network of wire effector component, a stirring means, a coil, a blade, a loop, or a drug or pharmaceutical formulation.

5. The system of claim 1, wherein the effector component is an active component comprising one or more of an inflatable balloon, a deployable member, an agent delivery module, an optical component, an ultrasonic component, an electric component, a magnetic component, a fluidic component, a pneumatic component, a chemical component, a mechanical component, or a drug or pharmaceutical delivery lumen.

6. The system of claim 1 wherein the first deployable or expandable component and the second deployable or expandable component are each independently selected from a group consisting of an isolation balloon and a deployable netting.

7. The system of claim 1 wherein the first deployable or expandable component is a first isolation balloon and the second deployable or expandable component is a second isolation balloon.

8. The system of claim 5, further comprising an active component control connector coupled to the active component, the active component control connector being configured to actuate the active component.

9. A concentric cylinder effector deployment system comprising:
a concentric cylinder system comprising:
   an inner shaft having an inner shaft distal tip and a first deployable or expandable component positioned proximate to the inner shaft distal tip, and
   an outer shaft approximately concentric with and surrounding at least a portion of the inner shaft, and having an outer shaft distal tip and a second deployable or expandable component positioned proximate to the outer shaft distal tip; and
an effector deployment system configured to be attached to the concentric cylinder system and comprising:
   a mounting element configured to slidably couple to the inner shaft between the first deployable or expandable component and the second deployable or expandable component;
   an effector component configured to couple to the mounting element and to perform a procedure on a portion of tissue proximate to a localized target zone that extends from the outer shaft distal tip to the inner shaft distal tip; and
   a feeder linkage configured to couple to a proximal portion of the mounting element and to apply a force to advance or retract the mounting element along at least a portion of the inner shaft; and an applicator configured to mount and to remove the effector component to and from the inner shaft.

10. The system of claim 9, wherein the mounting element is a cart, and wherein the cart comprises at least one circling element configured to surround a portion of the inner shaft and is removable from the inner shaft.

11. The system of claim 9, wherein the effector component is a passive component comprising one or more of a spiral, a mesh or a network of wire effector component, a stirring means, a coil, a blade, a loop, or a drug or pharmaceutical formulation.

12. The system of claim 9, wherein the effector component is an active component comprising one or more of an inflatable balloon, a deployable member, an agent delivery module, an optical component, an ultrasonic component, an electric component, a magnetic component, a fluidic component, a pneumatic component, a chemical component, a mechanical component, or a drug or pharmaceutical delivery lumen.

13. The system of claim 9, wherein the feeder linkage comprises one or more of a stiff wire, a rhombus or scissor linkage, a telescoping line, or a series of rigid or semi-rigid links.

14. The system of claim 9, wherein the mounting element is a bus, and wherein the bus is attached to the inner shaft.

15. The system of claim 9 wherein the first deployable or expandable component and the second deployable or expandable component are each independently selected from a group consisting of an isolation balloon and a deployable netting.

16. The system of claim 9 wherein the first deployable or expandable component is a first isolation balloon and the second deployable or expandable component is a second isolation balloon.

17. The system of claim 12, further comprising an active component control connector coupled to the active component, the active component control connector being configured to actuate the active component.

18. The system of claim 14, further comprising a socket means configured to couple the feeder linkage to the bus.

19. The system of claim 18, wherein the socket means comprises:
a first socket unit; and
a second socket unit;
wherein:
the first socket unit is configured to form an attachment with the second socket unit;
the first socket unit is attached to a portion of the bus; and
the second socket unit is attached to a distal portion of the feeder linkage.

20. A concentric cylinder effector deployment system comprising:
a concentric cylinder system comprising:
an inner shaft having an inner shaft distal tip and a first deployable or expandable component positioned proximate to the inner shaft distal tip, and
an outer shaft approximately concentric with and surrounding at least a portion of the inner shaft, and having an outer shaft distal tip and a second deployable or expandable component positioned proximate to the outer shaft distal tip; and
an effector deployment system configured to be attached to the concentric cylinder system, and comprising:
a cart configured to slidably couple to the inner shaft between the first deployable or expandable component and the second deployable or expandable component;
an effector component configured to couple to the cart and to perform a procedure on a portion of tissue in a localized target zone, the localized target zone extending from the outer shaft distal tip to the inner shaft distal tip;
a feeder linkage configured to couple to the cart and to apply a force to advance or retract the cart along at least a portion of the inner shaft; and
an applicator configured to mount and to remove the cart to and from the inner shaft.

21. The system of claim 20, wherein the cart comprises at least one circling element configured to surround a portion of the inner shaft and is removable from the inner shaft.

22. The system of claim 20, wherein the effector component is a passive component comprising one or more of a spiral, a mesh or a network of wire effector component, a stirring means, a coil, a blade, a loop, or a drug or pharmaceutical formulation.

23. The system of claim 20, wherein the effector means is an active component comprising one or more of an inflatable balloon, a deployable member, an agent delivery module, an optical component, an ultrasonic component, an electric component, a magnetic component, a fluidic component, a pneumatic component, a chemical component, a mechanical component, or a drug or pharmaceutical delivery lumen.

24. The system of claim 20, wherein the feeder linkage comprises one or more of a stiff wire, a rhombus or scissor linkage, a telescoping line, or a series of rigid or semi-rigid links.

25. The system of claim 20, wherein the applicator comprises a distal portion configured to couple to the cart and to mount the cart to the inner shaft.

26. The system of claim 20 wherein the first deployable or expandable component and the second deployable or expandable component are each independently selected from a group consisting of an isolation balloon and a deployable netting.

27. The system of claim 20 wherein the first deployable or expandable component is a first isolation balloon and the second deployable or expandable component is a second isolation balloon.

28. The system of claim 23, further comprising an active component control connector coupled to the active component, the active component control connector being configured to actuate the active component.

29. The system of claim 25, wherein applicator further comprises an extended portion having a narrower lateral dimension than the inner shaft of the concentric cylinder system.

* * * * *

UNITED STATES PATENT AND TRADEMARK OFFICE
CERTIFICATE OF CORRECTION

PATENT NO. : 11,134,965 B2
APPLICATION NO. : 15/006706
DATED : October 5, 2021
INVENTOR(S) : John R. Gilbert It is certified that error appears in the above-identified patent and that said Letters Patent is hereby corrected as shown below:

In the Claims

At Claim 1, Column 17, Line 64, delete "and".

At Claim 9, Column 18, Line 59, delete "and".

At Claim 9, Column 18, Line 63, insert a return and indent beginning with "and an applicator config-".

Signed and Sealed this
Twenty-eighth Day of June, 2022

*Katherine Kelly Vidal*

Katherine Kelly Vidal
*Director of the United States Patent and Trademark Office*